US009951398B2

(12) United States Patent
Auxier, II et al.

(10) Patent No.: US 9,951,398 B2
(45) Date of Patent: Apr. 24, 2018

(54) METHODS FOR GAS-PHASE THERMOCHROMATOGRAPHIC SEPARATIONS OF FISSION AND ACTIVATION PRODUCTS

(71) Applicant: University of Tennessee Research Foundation, Knoxville, TN (US)

(72) Inventors: John D. Auxier, II, Knoxville, TN (US); Daniel Hanson, Aiken, SC (US); Matthew L. Marsh, Knoxville, TN (US); Howard L. Hall, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 107 days.

(21) Appl. No.: 14/807,463

(22) Filed: Jul. 23, 2015

(65) Prior Publication Data

US 2016/0024617 A1 Jan. 28, 2016

Related U.S. Application Data

(60) Provisional application No. 62/150,398, filed on Apr. 21, 2015, provisional application No. 62/028,199, filed on Jul. 23, 2014.

(51) Int. Cl.
| | |
|---|---|
| *A61K 9/00* | (2006.01) |
| *C22B 59/00* | (2006.01) |
| *C22B 7/00* | (2006.01) |
| *G01N 30/12* | (2006.01) |
| *G21F 9/02* | (2006.01) |
| *G21F 9/04* | (2006.01) |

(Continued)

(52) U.S. Cl.
CPC .............. *C22B 59/00* (2013.01); *C22B 7/007* (2013.01); *G01N 30/12* (2013.01); *G21F 9/02* (2013.01); *G21F 9/04* (2013.01); *G21F 9/28* (2013.01); *G01N 2030/025* (2013.01)

(58) Field of Classification Search
CPC ...................................................... C22B 59/00
See application file for complete search history.

(56) References Cited

U.S. PATENT DOCUMENTS

2013/0069040 A1    3/2013  Hong et al.

OTHER PUBLICATIONS

Stites, The Rare Earth Metals and their Compounds VIII. An Improved Method for the Synthesis of Some Rare Earth Acetylacetonates, J. Am. Chem. Soc., 1948, 70, 3142-3143.*

(Continued)

*Primary Examiner* — Paul W Dickinson
(74) *Attorney, Agent, or Firm* — Jenkins, Wilson, Taylor & Hunt, P.A.

(57) ABSTRACT

Methods are provided for characterizing samples containing chemical elements such as rare earth elements, actinides, and heavy transition metals by treating the samples to form volatile complexes of the elements (e.g., β-diketonate complexes or other organic ligand complexes of the elements) and then analyzing the complexes, for example, via gas-phase thermochromatography. Also provided are methods for separating and/or recovering such chemical elements. The methods produce less waste and can be performed more rapidly than conventional liquid extraction methods and can provide separated elements of high purity (e.g., 99.9999% purity).

19 Claims, 13 Drawing Sheets

1,1,1,5,5,5 – hexafluoro – 2,4 – pentadione 2,2,6,6-tetramethyl-3,5-heptanedione 6,6,7,7,8,8,8-heptafluoro-2,2-dimethyl-3,5-octanedione

(51) Int. Cl.
  *G21F 9/28* (2006.01)
  *G01N 30/02* (2006.01)

(56) References Cited

OTHER PUBLICATIONS

Amano et al., "Sublimation Behavior of Tris(2,2,6,6-tetramethyl-3,5-heptanedionato_lanthanoid(III)," Bull, Chem. Soc. Jpn., vol. 54, No. 5, pp. 1368-1374, (1981).

Auxier et al., "Thermochromatographic Analysis of Volatile Organometallic Fission Products," Abstract for Presentation at the Tenth International Conference on Methods and Applications of Radioanalytical Chemistry, Kailua-Kona, Hawaii, Apr. 12-17, 2015, MARC X Final Books of Abstracts, Log: 533, p. 278 (Mar. 15, 2015).

Auxier et al., "Thermochromatographic Analysis of Volatile Organometallic Fission Products," Slides for Presentation at the Tenth International Conference on Methods and Applications of Radioanalytical Chemistry, Kailua-Kona, Hawaii, pp. 1-34 (Apr. 17, 2015).

Becht et al., "Some Cerium β-Diketonate Deriratives as MOCVD Precursors," Chem. Mater., 5(1), pp. 137-144 (1993).

Berg et al., "Fractional Sublimation of the β-Diketone Chelates of the Lanthanide and Related Elements," Anal. Chim. Acta., 40, pp. 101-113 (1968).

Coats et al., Kinetic Parameters from Thermogravimetric Data II.,: Polymer Letters, vol. 3, pp. 917-920 (1965).

Elsentraut et al., "Volitile Rare Earth Chelates", J. Am. Chem. Soc., vol. 87(22), pp. 5254-5256 (Nov. 20, 1965).

Fahey et al., "Postdetonation nuclear debris for attribution," Proc. Natl. Acad. Sci., vol. 107, No. 47, pp. 20207-20212 (Nov. 23, 2010).

Freeman et al., "Interpretation of the Kinetics of Thermogravimetric Analysis,"J. Phys. Chem., 73(3), pp. 751-751 (1969).

Garrison et al., "Monte Carlo analysis of Thermochromatography as a fast separation menthod for nucler forensics", J. Radioanal. Nucl. Chem., 291, pp. 885-894 (2012).

Halls and Auxier, Exploring Rapid Radiochemical Separators at the University of Tennessee Radiochemistry Center of Excellence, Abstract for presentation at the Tenth International Conference on Methods and Applications of Radioanalytical Chemistry, Kailua-Kona, Hawaii, Apr. 12-17, 2015, MARC X Final Book of Abstracts, Log: 439, p. 219 (Mar. 15, 2015).

Hammond, et al., "Chelates of β-Diketones. V. Preparation and Properties of Chelates Contailing Sterically Hindered Ligands," Inorg. Chem., vol. 2(1), pp. 73-76 (Feb. 1963).

Hanson et al., "Assessing thermochromatography as a separation method for nuclear forensics: current capability vis-à-vis forensic requirements," J. Radioanal. Nucl. Chem., 289(1), 213-223 (2011).

Horowitz et al., "A New Analysis of Thermogravimetric Traces," Anal. Chem., vol. 35(10), pp. 1464-1468 (Sep. 1963).

Richardson et al., "Rare-Earth Trishexaflouroacetylacetonates and Related Compounds," J. Inorg. Nucl. Chem., vol. 30, pp. 1275-1289 (1968).

Richardson et al., "Volatile Rare Earth Chelates of 1,1,1,5,5,5-Hexafluoro-2,4-pentanedione and 1,1,1,2,2,3,3,7,7,7,-Decafluoro-4,6-heptanediene," Inorg. Chem., vol. 10(3), pp. 498-504 (1971).

Selbin et al., "Preparation and Properties of Lanthanide Chelate Complexes", Inorg. Chem., 10(7), pp. 1383-1387 (1971).

Shannon et al., "Revised Effective Ionic Radii and Systematic Studies of Interatomic Distances in Halides and Chalcogenides," Acta Cryst., vol. 32 pp. 751-767, (1976).

Sharp et al., "Rapid analysis of trinitite with nuclear forensic applications for post-detonation material analysis," J. Radioanal. Nucl. Chem., vol. 302, pp. 57-67(Jul. 10, 2014).

Springer et al., "Rare Earth Chelates for 1,1,1,2,2,3,3-Heptafluoro-7,7-dimethyl-4, 6-octanedione," Inorg. Chem., 6(6), pp. 1105-1110 (Jun. 1967).

Stratz et al., "Experimental Derivation of VIlatice Lanthanide Thermodynamic Properties for Rapid Gas-Phase Separation Optimization,"Abstract for poster at the Tenth International Conference on Methods and Applications of Radioanalytical Chemistry, Kailua-Kona, Hawaii, Apr. 12-17, 2015, MARC X Final Book of Abstracts, Log. 561, p. 300 (Mar. 15, 2015).

Utsunomiya and Shigematsu, "Thermogravimetric and Gas-Chromatographic Study of Neodymium, Gadolinum and Erbium β-Diketone Chelates," Anal., Chim. Acta, 58(2), pp. 411-419 (1972).

Auxier et al., "Gas-phase Thermochromatographic Separations of Fission and Activation Products" Conference paper for the 2014 Meeting of the Institute for Nuclear Materials Management (INMM), Report No. 14-A-519-INMM, Jun. 9, 2014 (pp. 1-9).

Auxier et al. (2016a) Gas-phase detection of solid-state fission product complexes for post-detonation nuclear forensic analysis. J Radioanal Nucl Chem 310:1273-1276.

Auxier et al. (2016b) Themodynamic analysis of volatile organometallic fission products. J Radioanal Nucl Chem 307:1621-1627.

Hall and Auxier (2016) Exploring rapid radiochemical separations at the University of Tennessee Radiochemistry Center of Excellence. J Radioanal Nucl Chem 307:1723-1727.

Shahbazi et al. (2017) Characterization and thermogravimetric analysis of lanthanide hexafluoroacetylacetone chelates. J Radioanal Nucl Chem 311:617-626.

Stratz et al. (2017) Gas chemical adsorption characterization of lanthanide hexafluoracetylacetonates. J Radioanal Nucl Chem 312:355:360.

* cited by examiner

METHODS FOR GAS-PHASE THERMOCHROMATOGRAPHIC SEPARATIONS OF FISSION AND ACTIVATION PRODUCTS

RELATED APPLICATIONS

The presently disclosed subject matter is based on and claims the benefit of U.S. Provisional Patent Application Ser. No. 62/028,199, filed Jul. 23, 2014; and U.S. Provisional Patent Application Ser. No. 62/150,398, filed Apr. 21, 2015, the disclosure of each of which is incorporated herein by reference in its entirety.

GOVERNMENT INTEREST

This invention was made with government support under Grant No. DE-NA0001983 awarded by the National Nuclear Security Administration. The government has certain rights in the invention.

TECHNICAL FIELD

The presently disclosed subject matter relates to methods of characterizing, separating and/or recovering chemical elements, such as rare earth elements, using gas-phase thermochromatography. Materials containing atoms of the chemical elements can be treated to provide volatile complexes of the elements with ligands such as β-diketonates and the volatile complexes analyzed, separated and/or recovered, such as via gas-phase chromatography, optionally in combination with mass spectrometry.

ABBREVIATIONS

° C.=degrees Celsius
%=percentage
amu=atomic mass unit
ATR=attenuated total reflectance
aq=aqueous
C=carbon
cm=centimeter
Dy=dysprosium
F=fluoride
FT=Fourier transform
GC=gas chromatography
H=hydrogen
hdpm=diketonate of 2,2,6,6-tetramethyl-3,5-heptane-dione
Hfac=1,1,1,5,5,5-hexafluoroacetyl-acetonate (diketonate of 1,1,1,5,5,5-hexafluoro-2,4-pentadione)
Hfod=diketonate of 6,6,7,7,8,8,8-heptafluoro-2,2-dimethyl-3,5-octanedione
IC=inductively coupled
IR=infrared
l=liquid
K=Kelvin
Ln=lanthanide
MHz=megaHertz
min=minute
mL=milliliters
mmol=millimole
MS=mass spectrometry
NMR=nuclear magnetic resonance
REE=rare earth element
s=solid
sec=second
Sm=samarium
TCD=thermal conductivity detector
Tm=thullium
TOF=time-of-flight
$t_r$=retention time
Z=atomic number

BACKGROUND

Fission and activation products appearing in nuclear debris typically include transition metals and rare earth elements (REEs). Separation and characterization of the transition metal and REE content of this type of debris (e.g., taken from dust near nuclear facilities or from the sites of nuclear or suspected nuclear explosions) can offer information regarding the provenance, trafficking, and enrichment of nuclear materials. Thus, the ability to perform rapid separations, for example, in a post nuclear weapon detonation situation, is an important aspect of national security. The characterization of fission and activation products can hold clues to the construction details of a detonated weapon, which can assist in the overall investigation of a nuclear event for the purpose of attribution of the attack. However, current chemical separation methods for fission and activation products can require liquid phase separations that can take as long as a week and result in significant amounts of waste.

REEs also find use in a number of electronic and other high technology devices. For example, iPods and similar devices can contain dysprosium, neodymium, praseodymium, samarium, and terbium. Fibre-optics and energy-efficient light bulbs can include europium, terbium and yttrium. Wind turbines and hybrid vehicles can also include various REEs. In view of growing concern over the increasing amount of waste from these types of devices, as well as due to increases in demand and rising costs for REEs, there is an increased interest in efficient methods for separating and recovering REEs, e.g. so that they can be more efficiently produced from REE-containing ores and/or so that they can be recycled from manufacturing or post-consumer waste.

Accordingly, there is a growing need for additional methods of separating, characterizing, and recovering rare earth and related chemical elements. In particular, there is a need for efficient and accurate methods that can be performed rapidly, that are easy to perform, and/or which are environmentally friendly.

SUMMARY

In some embodiments, the presently disclosed subject matter provides a method for characterizing a sample comprising a compound or compounds comprising atoms of one or more chemical elements, wherein each of said one or more chemical elements is selected from the group consisting of a rare earth element, uranium (U), thorium (Th), an actinide, and a heavy transition metal; the method comprising: (a) providing a sample comprising a compound or compounds comprising atoms of said one or more chemical elements; (b) forming a complex of each of said one or more chemical elements, wherein the complex comprises a ligand and one of said one or more chemical elements; (c) volatizing the complex of each of said one or more chemical elements; and (d) determining the identity of the one or more chemical elements, wherein the determining for each of the one or more chemical elements is based upon a retention time of a volatized complex on a gas chromatography column or upon a temperature of volatilization of a complex.

In some embodiments, the sample comprises an oxide of each of the one or more chemical elements. In some embodiments, each of the one or more chemical elements is a rare earth element selected from the group comprising cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

In some embodiments, the ligand is selected from the group comprising a ketone, an enolate, a polyketone, a polyketonate, a β-diketonate, an ether, a polyether, and a polyalcohol. In some embodiments, step (b) comprises: (i) contacting the sample with a strong acid to form a salt of each of the one or more chemical elements; and (ii) contacting the salt of each of the one or more chemical elements with a ligand.

In some embodiments, the strong acid comprises hydrochloric acid and the salt of each of the one or more chemical elements is a hydrochloride salt. In some embodiments, the strong acid further comprises one or more of nitric acid, hydrofluoric acid, and sulfuric acid.

In some embodiments, the ligand is a β-diketonate, and the β-diketonate is provided as an ammonium salt. In some embodiments, the β-diketonate is provided in at least about a 4 molar excess compared to the salt. In some embodiments, the ligand is a β-diketonate selected from the group comprising the diketonate of acetylacetone, the diketonate of 1,1,1,5,5,5-hexafluoroacetylacetone (hfac), the diketonate of 6,6,7,7,8,8-heptafluoro-2,2-dimethyl-3,5-oxtanedione (hfod); and the diketonate of 2,2,6,6-tetramethyl-3,5-heptanedione (hdpm).

In some embodiments, each complex of the one or more chemical elements volatizes at a temperature of about 250° C. or less. In some embodiments, the determining of step (d) comprises comparing the retention time of the complex(s) to a previously determined retention time for one or more complexes of the ligand and a known chemical element.

In some embodiments, the sample comprises a compound or compounds comprising atoms of at least two chemical elements selected from the group comprising a rare earth element, uranium (U), thorium (Th), an actinide, and a heavy transition metal. In some embodiments, the sample is a sample comprising nuclear fission and/or activation products.

In some embodiments, the method further comprises determining a mass spectrum of one or more volatilized complex following desorption of the complex from a gas chromatography column. In some embodiments, the method further comprises collecting one or more complex desorbed from a gas chromatography column, thereby recovering the one or more chemical elements.

In some embodiments, the presently disclosed subject matter provides a method of separating a mixture comprising atoms of at least two chemical elements, wherein each of said at least two chemical elements is selected from the group consisting of a rare earth element, uranium (U), thorium (Th), an actinide, and a heavy transition metal; the method comprising: (a) providing a sample comprising a compound or compounds comprising atoms of at least two of said chemical elements; (b) forming a mixture comprising a complex of each of the at least two chemical elements, wherein each complex comprises one of the at least two chemical elements and a ligand; and (c) volatizing the complexes of the mixture of step (b), thereby separating the complexes. In some embodiments, step (c) comprises heating the mixture slowly to separate the mixture based on differences in volatilization temperature. In some embodiments, step (c) comprises heating the mixture to a predetermined temperature to volatize each of the complexes in the mixture and applying the volatized mixture to a gas chromatography column.

In some embodiments, the ligand is selected from the group comprising a ketone, an enolate, a polyketone, a polyketonate, a β-diketonate, an ether, a polyether, and a polyalcohol. In some embodiments, the sample comprises an oxide of each of the at least two chemical elements. In some embodiments, each of the at least two chemical elements is a rare earth element selected from the group comprising Ce, Dy, Er, Eu, Gd, Ho, La, Lu, Nd, Pr, Pm, Sm, Sc, Tb, Tm, Yb, and Y. In some embodiments, the sample is a sample comprising nuclear fission and/or activation products or is a sample comprising waste from electronic and/or high technology products.

In some embodiments, step (b) comprises: (i) contacting the sample with a strong acid to form a mixture of salts, wherein the mixture comprises a salt of each of the at least two chemical elements, and (ii) contacting the mixture of salts with a ligand to provide a mixture of complexes, wherein the mixture of complexes comprises a complex of each of the at least two chemical elements and the ligand. In some embodiments, the strong acid comprises hydrochloric acid and the mixture of salts comprises a mixture of hydrochloride salts. In some embodiments, the strong acid further comprises one or more of nitric acid, hydrofluoric acid, and sulfuric acid.

In some embodiments, the ligand is a β-diketonate and the β-diketonate is provided as an ammonium salt. In some embodiments, the β-diketonate is provided in about a 4 molar excess compared to the salts. In some embodiments, the ligand is a β-diketonate selected from the group comprising the diketonate of acetylacetone, the diketonate of 1,1,1,5,5,5-hexafluoroacetylacetone (hfac), the diketonate of 6,6,7,7,8,8-heptafluoro-2,2-dimethyl-3,5-oxtanedione (hfod); or the diketonate of 2,2,6,6-tetramethyl-3,5-heptanedione (hdpm).

In some embodiments, each complex formed in step (b) volatizes at a temperature of about 250° C. or less. In some embodiments, the method further comprises collecting at least one separated complex.

In some embodiments, the presently disclosed subject matter provides a method of recovering a rare earth element from waste, the method comprising: (a) providing waste material comprising atoms of at least one rare earth element; (b) treating the waste material to provide a complex of each of the at least one rare earth element, wherein each complex further comprises a ligand; (c) volatizing the complex of each of the at least one rare earth element; (d) contacting the volatized complex of each of the at least one rare earth element with a gas chromatography column or with a collection surface; and (e) collecting at least one complex when it desorbs from a gas chromatography column or after it condenses on a collection surface; thereby recovering a rare earth element.

In some embodiments, the waste material comprises nuclear fission and/or activation products or waste from electronic and/or high technology products. In some embodiments, the waste material comprises at least two rare earth elements, and the volatized complex of each of the at least two rare earth elements has a different retention time on a gas chromatography column and/or a different volatilization temperature. In some embodiments, the ligand is selected from the group comprising a ketone, an enolate, a polyketone, a polyketonate, a β-diketonate, an ether, a polyether, and a polyalcohol.

Accordingly, it is an object of the presently disclosed subject matter to provide methods to characterize samples containing chemical elements, such as rare earth elements, heavy transition metals, and actinides; to separate the chemical elements in such samples, and/or to recover rare earth elements from such samples.

An object of the presently disclosed subject matter having been stated hereinabove, and which is achieved in whole or in part by the presently disclosed subject matter, other objects will become evident as the description proceeds hereinbelow.

DETAILED DESCRIPTION

Figure 1:
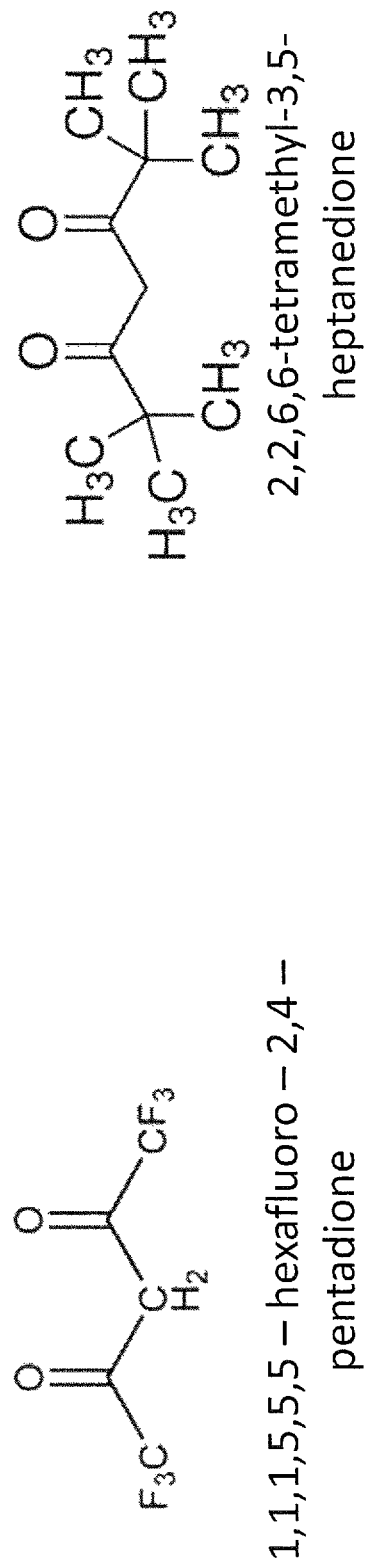
FIG. 1 is a schematic drawing of chemical structures of representative ligands, such as β-diketones, that can be used to provide ligands for the presently disclosed complexes. The structures include: 1,1,1,5,5,5-hexafluoro-2,4-pentadione (top left), 2,2,6,6-tetramethyl-3,5-heptanedione (top right), and 6,6,7,7,8,8,8-heptafluoro-2,2-dimethyl-3,5-octanedione (bottom).
Figure 1:
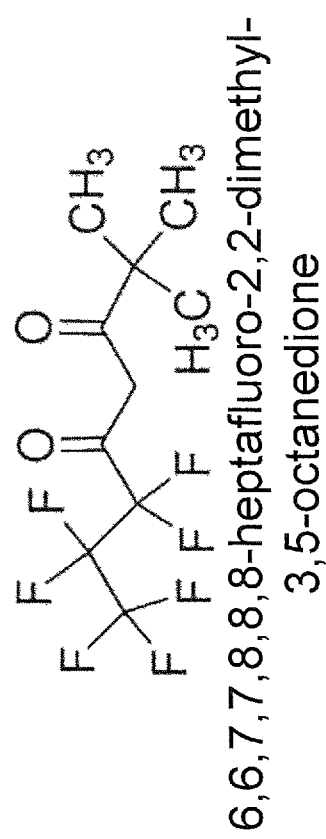

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

Unless otherwise indicated, all numbers expressing quantities of temperature, time, concentration, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

The term "atomic number" refers to the number of protons in the nucleus of an atom. Each chemical element has a unique atomic number (Z). Atoms with the same number of protons, but different numbers of neutrons have different atomic masses and are referred to as isotopes.

As used herein the terms "rare earth element" or "rare earth metal" refer to the seventeen chemical elements of the lanthanide series in addition to scandium (Sc) and yttrium (Y). Accordingly, the REE include cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y). Rare earth elements (REEs) can have useful magnetic, phosphorescent and catalytic properties.

The term "lanthanide" and the abbreviation "Ln" as used herein can refer to the fifteen chemical elements with Z=57-71, i.e., Ce, Dy, Er, Eu, Gd, Ho, La, Lu, Nd, Pr, Pm, Sm, Tb, Tm, and Yb. However, unless otherwise noted, the term lanthanide and the abbreviation Ln can also be used herein synonymously with rare earth element and REE.

The term "heavy transition metal" as used herein refers to transition metals with Z=72 or greater. Thus, the heavy transition metals include, for example, hafnium (Hf), tantalum (Ta), tungsten (W), rhenium (Rd), osmium (Os), iridium (Ir), platinum (Pt), gold (Au), mercury (Hg), rutherfordium (Rf), dubnium (Db), seaborgium (Sg), bohrium (Bh), hassium (Hs), and copernicium (Cn).

The term "actinide" refers to the fifteen chemical elements with Z=89-103. Thus, the actinides include actinium (Ac), thorium (Th), protactinium (Pa), uranium (U), neptunium (Np), plutonium (Pu), americium (Am), curium (Cm), berkelium (Bk), californium (Cf), einsteinium (Es), fermium (Fm), mendelevium (Md), nobelium (No), and lawrencium (Lr).

The term "salt" as used herein refers to a compound formed via an ionic interaction between a positively charged ion or ions (e.g., a metal ion) and a negatively charged ion or ions. The ions can be monoatomic (e.g., $Cl^-$ or $Na^+$) or polyatomic (e.g., $NO_3^-$). The ions can also be organic (i.e., include carbon atoms) or inorganic. The salt compound can have no net charge.

The terms "complex" and "coordination complex" as used herein refer to a compound in which there is a coordinate bond between a positively charged ion (e.g., a REE ion, actinide ion, or a transition metal ion) and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on positively charged ion (e.g., a REE, actinide, or transition metal ion) resulting in an attractive force between the electron pair donor and the ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a REE, actinide, or transition metal ion (e.g., in solution) to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

In some embodiments, the presently disclosed subject matter relates to complexes formed with organic ligands (i.e., ligands including one or more carbon atom), such as, ketones, including di- and polyketones, and their anions (e.g., enolates, β-diketonates, and other polyketonates), amines, ethers, and polyalcohols. In some embodiments, the organic ligand is a β-diketonate ligand or ligands. The β-diketonate ligands can be formed via the abstraction of a hydrogen atom from a β-diketone, i.e., a compound having a moiety with the structure R'—C(=O)—CHR—C(=O)—R", wherein each of R, R', and R" is independently H or an alkyl, aralkyl or aryl group, optionally substituted with an alkyl or aryl group substituent(s).

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Aralkyl" refers to an -alkyl-aryl group or -aryl-alkyl group, optionally wherein the alkyl and/or aryl moiety is substituted.

The term "ketone" refers to a compound having the structure R—C(=O)—R', wherein R and R' are each independently alkyl, aralkyl, and aryl, optionally substituted with one or more alkyl and/or aryl group substituent(s). The term "polyketone" refers to a ketone comprising more than one —C(=O)— moiety. Polyketones can include diketones (e.g., ketones with two —C(=O)— moieties, including β-diketones), triketones, tetraketones, and the like.

The term "amine" as used herein can refer to a compound having the formula $N(R)_3$, wherein each R is independently selected from H, alkyl, aryl, and aralkyl, optionally substituted with one or more alkyl or aryl group substituent(s). In some embodiments, at least one R is alkyl, aryl, or aralkyl.

The term "ether" refers to compounds comprising the formula R—O—R', wherein R and R' are independently selected from alkyl, aralkyl, and aryl, optionally substituted by one or more alkyl or aryl group substituent(s). Ethers can include "polyethers", i.e., compounds comprising more than one —C—O—C-moiety. Polyethers can be linear or cyclic (e.g., crown ethers).

The terms "polyalcohol" or "polyol" refers to a compound comprising two or more —OH moieties. Polyalcohols can be aliphatic or aromatic. Polyalcohols can include, for example, glycols, such as ethylene or propylene glycol, polyphenols, and compounds that include hydroxyl-substituted phenol(s).

The term "halide" as used herein can refer to —Cl, —F, —Br, or —I.

The term "strong acid" refers to an acid that essentially ionizes 100% in water or an aqueous solution. Strong acids are compounds that have a pKa of <about −1 or of about −1.74 or less. Strong acids include, but are not limited to, hydrochloric acid (HCl), hydrobromic acid (HBr), hydroiodic acid (HI), perchloric acid ($HClO_4$), nitric acid ($HNO_3$), and sulfuric acid ($H_2SO_4$).

The term "volatized", and grammatical variations thereof, as used herein refers to vaporizing a chemical compound or complex without causing its decomposition.

II. General Considerations

Conventional radiochemical analysis performed as part of nuclear forensics processes can involve separations that often require extensive sample preparation involving lengthy solution phase separations. These separations can sometimes require several days (e.g., one week).

The presently disclosed subject matter relates, in some aspects, to the exploitation of gas-phase chemistry for the characterization, separation, and/or recovery of chemical elements typically present in fission and/or activation products, radiopharmaceuticals, electronic and/or high technology product waste, e.g., rare earth elements (REEs), actinides (e.g., uranium and thorium), and heavy transition metals. For example, in some embodiments, the presently disclosed subject matter relates to the preparation of volatile complexes of chemical elements from samples, followed by gas-phase thermochromatographic separation or sublimation. The separation or sublimation can be followed by detection via an approach such as time-of-flight mass spectrometry (TOF-MS).

For example, as described herein, REE complexes of β-diketonates can be readily volatized at temperatures at or below 250° C. The vaporized complexes can then be separated by gas chromatography (e.g., gas-liquid or gas-solid chromatography). Accordingly, the presently disclosed subject matter can provide liquid carrier-free separations and elemental and isotopic composition information regarding a given sample in a few hours (e.g., about 8 hours). The presently disclosed methods can also provide very pure separation products (e.g., 99.9999% pure), above the purity required for electronics (i.e., 99.999%).

Figure 4:
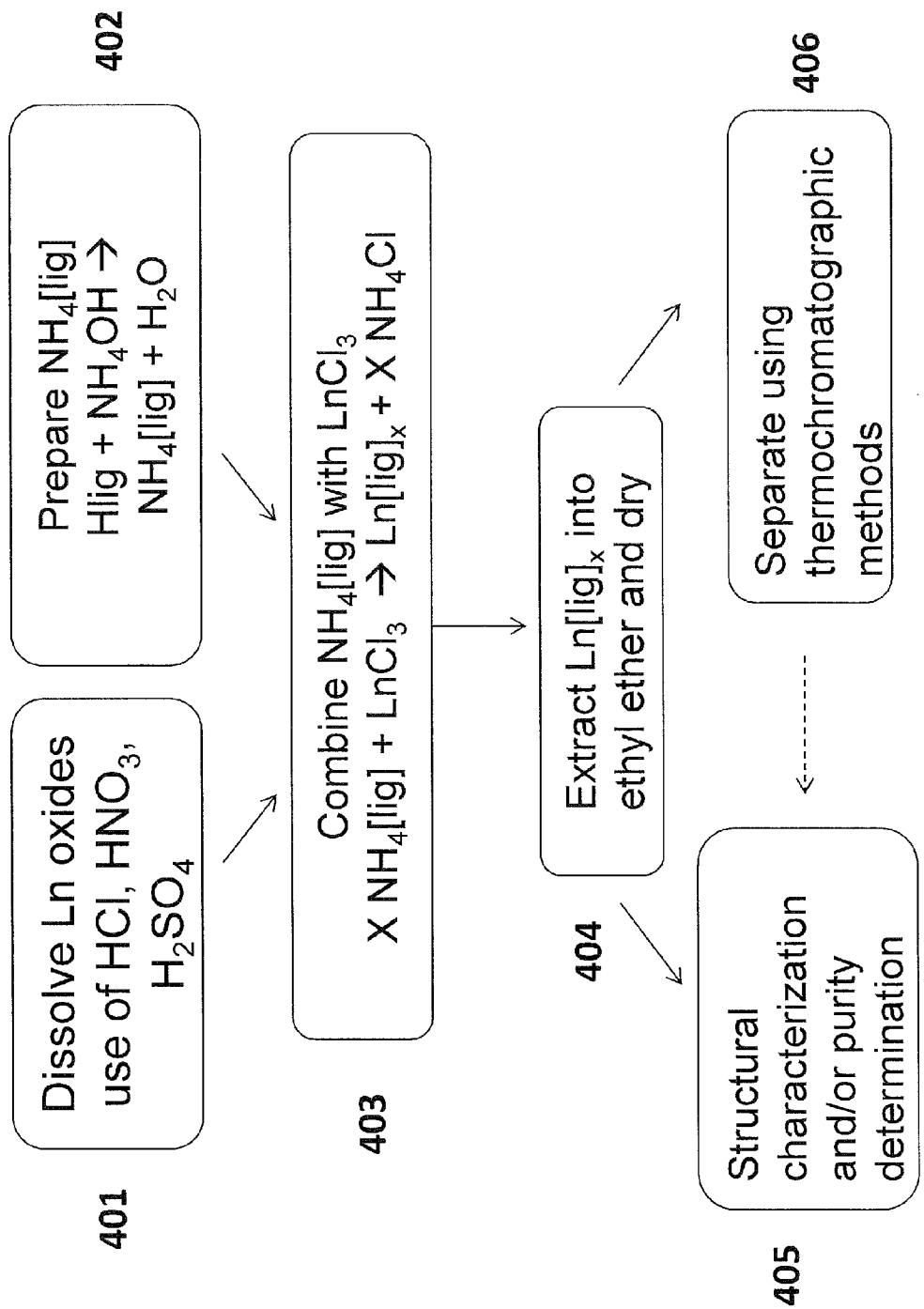
FIG. 4 is a schematic diagram of a method for the rapid separation and/or characterization of a sample containing lanthanide oxides (Ln oxides).

FIG. 4 provides a flow chart of a representative method for the separation and characterization of samples of fission and/or activation products. While the flow chart of FIG. 4 focuses on methods involving a sample comprising a lanthanide or lanthanides, it can also be used for samples comprising REEs, actinides, heavy transitions metals, and mixtures thereof. As indicated in box 401 of FIG. 4, lanthanide oxides can be treated with strong acids (e.g., concentrated HCl, nitric acid, sulfuric acid, or combinations thereof) to obtain lanthanide salts (e.g., $LnCl_3$). The samples can also be treated with hydrofluoric acid (HF) to dissolve and remove any silicon (Si) and titanium (Ti) present.

These salts can then be combined with a suitable ligand, such as a β-diketonate, to form coordination complexes. β-diketonate ligands can be formed by reacting a β-diketone with an appropriate base, such as ammonium hydroxide or another hydroxide, e.g., sodium, lithium, or potassium hydroxide. For example, as shown in box 402 of FIG. 4, the ammonium salt of a ligand is prepared by reacting a ligand with an extractable hydrogen (i.e., Hlig of FIG. 4) with ammonium hydroxide ($NH_4OH$) to form an ammonium salt ($NH_4$[lig]) and water.

Figure 3:
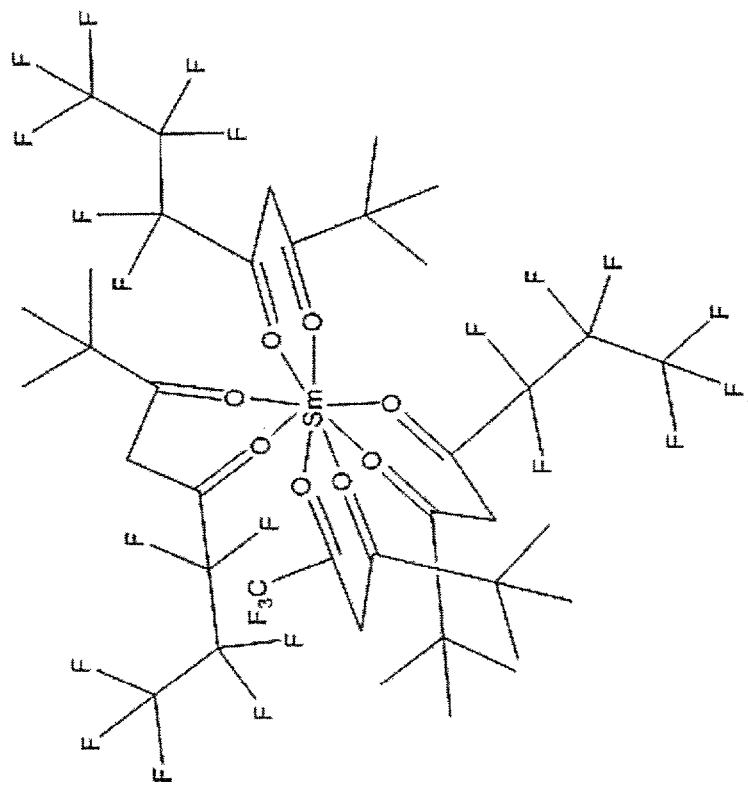
FIG. 3 is a schematic drawing of the chemical structure of a β-diketonate complex between samarium (Sm) and the β-diketonate of 6,6,7,7,8,8,8-heptafluoro-2,2-dimethyl-3,5-octanedione (Hfod).
Figure 2:
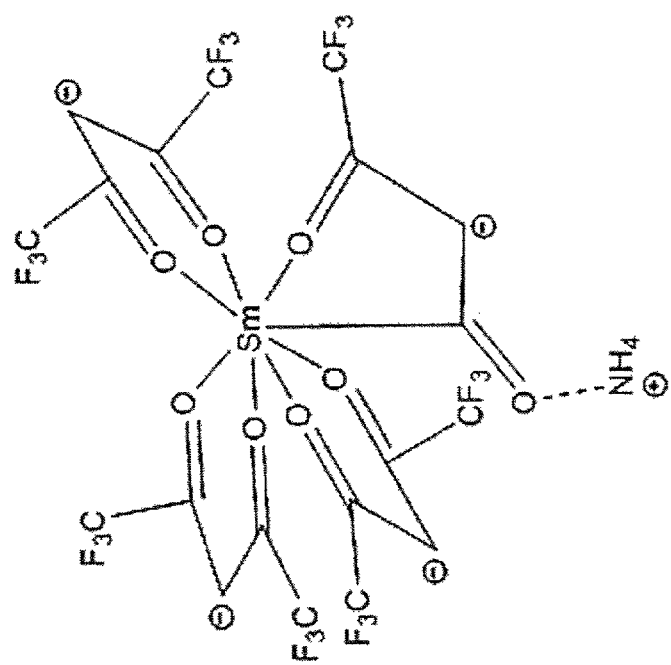
FIG. 2 is a schematic drawing of the chemical structure of a δ-diketonate complex between samarium (Sm) and 1,1,1,5,5,5-hexafluoro-2,4-acetylacetonate (Hfac).

Any suitable β-diketone can be used as the ligand precursor. In some embodiments, the β-diketone is one of the group comprising acetylacetone, 1,1,1,5,5,5-hexafluoroacetylacetone, 6,6,7,7,8,8-heptafluoro-2,2-dimethyl-3,5-oxtanedione, and 2,2,6,6-tetramethyl-3,5-heptanedione. FIG. 1 shows the chemical structures of some representative β-diketones. However, other β-diketones can also be used. The choice of β-diketone can be based on the desired volatility of the complex being formed (e.g., the lanthanide complex being formed). The volatility of this complex can be tailored by changing the functional group present at the gamma carbon of the β-diketone (e.g., changing an alkyl group to a halide, adding additional alkyl groups, etc.). Simple substitutions at the gamma carbon can shift the melting point of the complex formed by just a few degrees, while more complex substitutions can shift the melting point by more than 50° C. FIGS. 2 and 3 show chemical structures for some representative β-diketonate complexes.

In addition to β-diketonates, other ligands can also be used. For example, the ligand can be the β-diketone precursor itself. The ligand can also be another polyketone or anion thereof, i.e., a polyketonate. Further the ligand can be a compound with a single —C(=O)— moiety or anion thereof, e.g., a ketone or enolate. Suitable ligands also include ethers, polyethers (both linear or cyclic) and polyalcohols (e.g., glycols). The choice of ligand can be based on the desired volatility of the complex being formed (e.g., the lanthanide complex being formed). The volatility of the complexes can be tailored by changing the other functional groups present on the ligands. As would be understood by one of ordinary skill in the art upon a review of the instant disclosure, the ligands can be combined with the chemical element salts in any suitable form (e.g., as a salt or as a neutral compound or complex), depending upon the type of ligand and with any suitable stoichiometry, e.g., depending upon the expected formula of the complexes being formed.

Returning now to FIG. 4, Box 403 shows the combining of the ammonium salt of the ligand prepared in Box 402 with the lanthanide salts ($LnCl_3$) from the sample prepared in box 401 to form the lanthanide/ligand complexes (i.e., $Ln[lig]_x$) and ammonium chloride ($NH_4Cl$). The ammonium salt of the ligand can be provided in excess during the combining. For example, the ammonium ligand salt can be provided in about 3, 4, 5, 6, or more molar excess compared to the lanthanide salts (i.e., X of the equation in box 403 of FIG. 4 can be an integer such as 3, 4, 5, 6, or more). The number of ligands x that are present in each lanthanide complex formed can vary depending upon the Gibbs free energy for the reactions forming the different possible complexes of a particular lanthanide. In some embodiments, x is 3. In some embodiments, x is 4. In some embodiments, x is 5. In some embodiments, x is 6.

The lanthanide complexes can be extracted into an organic solvent, e.g., diethyl ether, and dried (e.g., in a desiccator and/or via evaporation under reduced pressure). See box 404 of FIG. 4. Then, the complexes can characterized (see box 405 of FIG. 4), separated (see box 406 of FIG. 4), or separated and then characterized (e.g., individually). Any useful characterization technique can be used to determine the type of lanthanide or lanthanides present, the isotopic ratios of that lanthanide, and/or other physical or structural information about the complex. Useful characterization techniques include, but are not limited to, infrared spectroscopy (e.g., FT-ATR-IR), powder x-ray diffraction (P-XRD) studies, single crystal x-ray diffraction studies (SC-XRD), mass spectrometry (e.g., ICP-TOF-MS), melting point determination, elemental analysis, and nuclear magnetic resonance (NMR).

Separation can involve gas-phase thermochromatographic methods, as indicated in Box 406 of FIG. 4. For example, a mixture containing a complex or complexes can be subjected to gas chromatography, e.g., by contacting the vaporized mixture with a gas chromatography column (e.g., comprising a liquid or solid stationary phase) under the flow of an inert or non-reactive gas (e.g., argon, helium, nitrogen, etc.). The column can be held at a desired temperature (e.g., between about 35° C. to about 250° C.) or the temperature can be increased in the column at a desired rate or rates. The column temperature or heating rate can be varied to increase separation of the complexes and/or to reduce the separation time. The gas flow rate can also be adjusted. Various stationary phases, column lengths, column diameters, and column packing materials can also be employed to affect separation. For example, a different column length or diameter can be selected to affect the separation of a mixture of complexes. By way of elaboration and not limitation, increasing length generally increases separation, while increasing diameter generally does the opposite.

Suitable column materials include, but are not limited to, steel, silica glass, quartz, and noble metals (e.g., platinum, gold, etc.). Column sizes can range from about 0.1 mm (e.g., as typical for a 30 m column) to megabore (i.e., large diameter, short columns containing bundles of capillary columns). The gas chromatography column can be a preparative column. The column stationary material can be selected to have a similar polarity as the complexes. In some embodiments, the stationary material in the column can be a material (e.g., a polysiloxane or polyethylene glycol-based material) typically used in the art for the separation of polar organic compounds. The thickness and/or identity of the stationary material can be varied to increase separation, as needed.

In some embodiments, separation is performed via sublimation, e.g., simple sublimation, vacuum sublimation, and/or fractional sublimation. Thus, in some embodiments, separation is performed by placing the complex or a mixture of complexes in a vessel and a heating the vessel gradually, optionally under vacuum or in the presence of a sweep gas, to vaporize the complex or complexes. The vessel can be in gaseous communication with a collection surface, e.g., a cold finger or the inside of a tube, upon which the vaporized complex or complexes can recondense. In some embodiments, the collection surface can be a glass surface. In some embodiments, the collection surface can be cooled (e.g., to a temperature below that of the vessel or to below room temperature). In some embodiments, the collection surface can be a tube and the temperature along the length of the tube can be controlled to provide one or more zones at different temperatures for recondensation of the vaporized complexes. Accordingly, in some embodiments, a mixture of complexes can be separated according to their different volatilities (e.g., based upon differences in the temperatures at which the complexes sublime).

Accordingly, in some embodiments, the presently disclosed subject matter provides a method for characterizing a sample comprising a compound or compounds comprising atoms of one or more chemical elements, wherein each of said one or more chemical elements is selected from the group consisting of a rare earth element, uranium (U), thorium (Th), an actinide, and a heavy transition metal. The method comprises preparing a complex of each of the one or more elements with a ligand. In some embodiments, the ligand can be an organic ligand, such as an organic ligand comprising an oxygen-based chelating moiety. In some embodiments, for example, the ligand can be a ketone, an enolate, a polyketone, a β-ketonate, a β-diketone, a polyketonate, an ether, a polyether, or a polyalcohol. The method can further comprise volatizing the complex. In some embodiments, the method can further comprise subjecting the complex or complexes to gas-phase thermochromatography. In some embodiments, the method can comprise subliming the complex. In some embodiments, the method comprises: (a) providing a sample comprising a compound or compounds comprising atoms of one or more chemical elements; (b) forming a complex of each of said one or more chemical elements, wherein the complex comprises a ligand on one of said one or more chemical elements; (c) volatizing the complex of each of said one or more chemical elements; and (d) determining the identity of one or more chemical elements, wherein the determining for each of the one or more chemical elements is based on a retention time of a volatized complex(s) on a gas chromatography column or upon a temperature of volatilization of a complex.

In some embodiments, the sample comprises an oxide of each of the one or more chemical elements. In some embodiments, each of the one or more chemical element is a REE (cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), or yttrium (Y)). In some embodiments, the sample can also comprise one or more actinides, such uranium or thorium.

In some embodiments, forming step (b) comprises contacting the sample with a strong acid to form a salt of each of the one or more chemical elements. The strong acid can comprise HCl, nitric acid, sulfuric acid, or a combination thereof. In some embodiments, the strong acid is provided in concentrated form. In some embodiments, the sample can also be contacted with HF to remove silicon or titanium. In some embodiments, the each salt is a hydrochloride salt. The salt or salts from the sample can then be contacted with a ligand. In some embodiments, the ligand is provided in excess (e.g., 2, 3, 4, 5, 6 or more molar excess compared to the salt of salts of the one or more chemical elements). In some embodiments, the ligand is provided as a salt.

In some embodiments, the ligand is a β-diketonate. Thus, in some embodiments, the method can comprise: (a) providing a sample comprising a compound or compounds comprising atoms of said one or more chemical elements; (b) forming a β-diketonate complex of each of said one or more chemical elements; (c) volatizing the β-diketonate complex of each of said one or more chemical elements; and (d) determining the identity of one or more chemical elements based upon the retention time of a volatized β-diketonate complex on a gas chromatography column or based upon the temperature of volatilization of a β-diketonate complex.

In some embodiments, the β-diketonate is provided as an ammonium salt. In some embodiments, the β-diketonate is provided as the salt of an alkali metal (e.g., sodium (Na), potassium (K), or lithium (Li)). Typically, a molar excess of the β-diketonate is combined with the salt or salts of the one or more chemical elements. In some embodiments, the β-diketonate is provided in at least about a 4 molar excess compared to the salt or salts of the one or more chemical elements. In some embodiments, the β-diketonate is provided in at least about a 6 molar excess compared to the salt or salts of the one or more chemical elements. In some embodiments, the β-diketonate is the diketonate of acetylacetone, the diketonate of 1,1,1,5,5,5-hexafluoroacetylacetone (hfac), the diketonate of 6,6,7,7,8,8-heptafluoro-2,2-dimethyl-3,5-oxtanedione (hfod); or the diketonate of 2,2,6,6-tetramethyl-3,5-heptanedione (hdpm).

In some embodiments, the β-diketonate (or other ligand) is provided in a solution comprising an organic solvent, such as an ether (e.g., diethyl ether) or an alcohol (e.g., ethanol). In some embodiments, the salt or salts are provided in an aqueous solution. The formed β-diketonate complexes or other ligand complexes can be extracted into an organic solvent (e.g., ether) and dried.

In some embodiments, each complex formed volatizes at a temperature of about 250° C. or less. In some embodiments, each complex volatizes at a temperature between about 250° C. and about 175° C. In some embodiments, each complex volatizes at a temperature of about 225° C. or less or of about 200° C. or less. Thus, in some embodiments, the volatizing is performed at a temperature of about 250° C., about 225° C., or about 200° C. or less.

In some embodiments, the volatizing of step (c) can further comprise contacting the volatized complex of each of said one or more chemical elements with a gas chromatography column. The contacting can be performed under the flow of an inert or non-reactive gas. In some embodiments, the gas is helium. In some embodiments, the gas chromatography column is at a first temperature (e.g., about 45° C.) and the temperature is increased to a second temperature (e.g., about 220°) at a desired rate or rates.

In some embodiments, the determining of step (d) comprises comparing the retention time of one or more complex on a gas chromatography column (i.e., under a particular set of temperature and other column conditions) to a previously determined retention time for one or more complexes of the ligand (such as a β-diketonate ligand) and a known chemical element. In some embodiments, the determining can comprise comparing the retention time of one or more complex to a calculated retention time. In some embodiments, the determining can further comprise determining a mass spectrum of one or more volatilized complex (such as a β-diketonate complex) following desorption of the complex from the gas chromatography column. In some embodiments, the determining can further comprise one or more of infrared spectroscopy, x-ray diffraction spectroscopy, nuclear magnetic resonance, elemental analysis, and melting point determination. In some embodiments, the method further comprises collecting one or more complex desorbed from the gas chromatography column, thereby recovering the one or more chemical elements. In some embodiments, the method can comprise collecting one or more recondensed complex from the collection surface of a sublimation apparatus (e.g., from a cold finger or the inside of a cooled tube).

In some embodiments, step (c) can be omitted and the determining step (d) is performed via one or more of mass spectroscopy, infrared spectroscopy, x-ray diffraction, nuclear magnetic resonance, elemental analysis, and melting point determination. In some embodiments, the sample comprises a compound or compounds comprising atoms of at least two chemical elements selected from the group consisting of a rare earth element, uranium (U), thorium (Th), an actinide, and a heavy transition metal. The presently disclosed characterization method can be performed rapidly (e.g., in less than about 24 hours, less than about 20 hours, less than about 16 hours, less than about 12 hours, less than about 8 hours), providing for the characterization of samples comprising short-lived compounds. In some embodiments, the sample is a sample comprising or suspected of comprising nuclear fission and/or activation products. In some embodiments, the sample comprises debris from a nuclear detonation. In some embodiments, the sample comprises spent fuel from a nuclear facility. In some embodiments, the sample comprises a raw ore (e.g., a newly mined ore) comprising one or more chemical elements. In some embodiments, the sample can comprise one or more radiopharmaceuticals (e.g., Zevalin®, Quadramet®, etc.). In some embodiments, the sample comprises electronics and/or high technology product waste.

In some embodiments, the presently disclosed subject matter provides a method of separating a mixture comprising atoms of at least two chemical elements, wherein each of said at least two chemical elements is selected from the group consisting of a rare earth element, uranium (U), thorium (Th), an actinide, and a heavy transition metal. The method can comprise preparing a complex of each of the chemical elements with a ligand and subjecting the complexes to gas-phase thermochromatography. In some embodiments, the method can comprise gas chromatography or sublimation. In some embodiments, the method can comprise: (a) providing a sample comprising a compound or compounds comprising atoms of at least two of said chemical elements; (b) forming a mixture comprising a complex of each of the at least two chemical elements, wherein each complex comprises one of the at least two chemical elements and a ligand; and (c) volatizing the complexes of the mixture of step (b), thereby separating the complexes. In some embodiments, step (c) can comprise heating the mixture slowly to separate the mixture based upon differences in volatilization temperatures. In some embodiments, step (c) can comprise heating the mixture to a pre-determined temperature (e.g., 250° C. or 225° C.) to volatize each of the complexes in the mixture and applying the volatized mixture to a gas chromatography column to separate the mixture via gas chromatography.

In some embodiments, the sample comprises an oxide of each of the at least two chemical elements. In some embodiments, each of the at least two chemical elements is a REE. The sample can be, for example, a sample comprising nuclear fission and/or activation products or a sample comprising waste from electronic and/or high technology products. The sample can be raw ore containing the chemical elements. The sample can be debris taken from the site of a nuclear detonation or spent nuclear fuel from a nuclear facility. The sample can comprise a radiopharmaceutical.

In some embodiments, the sample comprises two or three different chemical elements selected from REEs, actinides, and heavy transition metals. In some embodiments, the sample can comprise more than three different chemical elements, e.g., 4, 5, 6, 7, 8, or more chemical elements.

In some embodiments, step (b) comprises (i) contacting the sample with a strong acid to form a mixture of salts, wherein the mixture comprises a salt of each of the two or more chemical elements, and (ii) contacting the mixture of salts with a ligand to provide a mixture of complexes, wherein the mixture of complexes comprises a complex of each of the two or more chemical elements. The strong acid can comprise HCl, nitric acid, sulfuric acid, or a combination thereof. In some embodiments, the strong acid is provided in concentrated form. In some embodiments, the sample can also be contacted with HF to remove silicon or titanium. In some embodiments, each salt is a hydrochloride salt.

In some embodiments, the ligand is a β-diketonate. Thus, in some embodiments, the method can comprise: (a) providing a sample comprising a compound or compounds comprising atoms of two or more of said chemical elements; (b) forming a mixture comprising a β-diketonate complex of each of the two or more chemical elements; and (c) volatizing the β-diketonate complexes of the mixture of step (b). In some embodiments, the volatizing can comprise heating the mixture slowly to separate the mixture based on differences in volatilization temperature. In some embodiments, the method can comprise contacting the volatized β-diketonate complexes with a gas chromatography column, wherein each of the complexes desorbs from the column after a different amount of time, thereby separating the complexes.

In some embodiments, the β-diketonate (or other ligand) is provided as an ammonium salt. In some embodiments, the β-diketonate is provided as the salt of an alkali metal (e.g., sodium (Na), potassium (K), or lithium (Li)). In some embodiments, the β-diketonate (or other ligand) is combined with the salts of the two or more chemical elements where the β-diketonate (or other ligand) is in excess. In some embodiments, the β-diketonate (or other ligand) is provided in at least about a 4 molar excess compared to the salts of the two or more chemical elements. In some embodiments, the β-diketonate (or other ligand) is provided in at least about a 6 molar excess compared to the salts of the two or more chemical elements. In some embodiments, the β-diketonate is the diketonate of acetylacetone, the diketonate of 1,1,1, 5,5,5-hexafluoroacetylacetone (hfac), the diketonate of 6,6,7,7,8,8-heptafluoro-2,2-dimethyl-3,5-oxtanedione (hfod); or the diketonate of 2,2,6,6-tetramethyl-3,5-heptanedione (hdpm). In some embodiments, the diketonate (or other ligand) is provided in a solution with an organic solvent (e.g., an ether, such as diethyl ether, or an alcohol, such as ethanol). In some embodiments, the salts of the two or more chemical elements are provided in an aqueous solution. The formed complexes can be extracted into an organic solvent (e.g., ether) and dried.

In some embodiments, each complex volatizes at a temperature of about 250° C. or less. In some embodiments, each complex volatizes at a temperature between about 250° C. and about 175° C. In some embodiments, each complex volatizes at a temperature of about 225° C. or less or of about 200° C. or less. Thus, in some embodiments, the volatizing is performed at a temperature of about 250° C., about 225° C., or about 200° C. or less In embodiments comprising gas chromatography, the complexes can be contacted with a gas chromatography column under the flow of an inert or non-reactive gas. In some embodiments, the gas is helium. In some embodiments, the gas chromatography column is at a first temperature (e.g., about 45° C.) and the temperature is increased to a second temperature (e.g., about 220°) at a desired rate or rates.

In some embodiments, the method further comprising collecting at least one complex separated by and desorbed from the chromatography column. In some embodiments, the method further comprises collecting at least one complex from a collection surface. In some embodiments, the method further comprises performing mass spectrometry on at least one complex. In some embodiments, the method further comprises performing one or more additional characterization technique (e.g., NMR, elemental analysis, XRD, IR or melting point determination) on at least one complex.

In some embodiments, the presently disclosed subject matter provides a method of recovering a REE from waste. The method can comprise forming a volatile coordination complex of the REE and volatizing said complex. In some embodiments, the method comprises subjecting said complex to gas chromatography.

In some embodiments, the method comprises: (a) providing waste material comprising atoms of at least one rare earth element; (b) treating the waste material to provide a complex of each of the at least one rare earth element, wherein each complex further comprises a ligand; (c) volatizing the complex of each of the at least one rare earth element; (d) contacting the volatized complex of each of the at least one rare earth element with a gas chromatography column or a with a collection surface; and (e) collecting at least one volatized complex when it desorbs from the column or after it condenses on a collection surface; thereby recovering a rare earth element.

In some embodiment, the waste material comprises nuclear fission and/or activation products or waste from electronic and/or high technology products (e.g., iPods, smart phones or other cell phones, iPads or other tablet devices, computers, televisions, headphones, hybrid cars, electric cars, solar cells, batteries, fibre optics, energy efficient light bulbs, wind turbines, etc). In some embodiments, the waste material comprises at least two rare earth elements, and the volatized complex (such as a β-diketonate complex) of each of the at least two rare earth elements has a different retention time on the gas chromatography column.

In some embodiments, step (b) comprises (i) contacting the sample with a strong acid to form a salt of each of the at least one REE, and (ii) contacting the salt or salts with a ligand to provide a complex of each of the at least one REE. The strong acid can comprise HCl, nitric acid, sulfuric acid, or a combination thereof. In some embodiments, the strong acid is provided in concentrated form. In some embodiments, the sample can also be contacted with HF to remove silicon or titanium. In some embodiments, each salt is a hydrochloride salt.

In some embodiments, the ligand is a β-diketonate. Thus, in some embodiments, the method comprises (a) providing waste material comprising atoms of at least one rare earth element; (b) treating the waste material to provide a β-diketonate complex of each of the at least one rare earth element; (c) volatizing the β-diketonate complex of each of the at least one rare earth element; (d) contacting the volatized β-diketonate complex of each of the at least one rare earth element with a gas chromatography column or with a collection surface; and (e) collecting at least one volatized β-diketonate complex when it desorbs from the column or after it condenses on the collection surface; thereby recovering a rare earth element.

In some embodiments, the β-diketonate (or other ligand) is provided as an ammonium salt. In some embodiments, the β-diketonate (or other ligand) is provided as the salt of an alkali metal (e.g., sodium (Na), potassium (K), or lithium (Li)). Typically, the β-diketonate or other ligand is combined with the salt of the at least one REE where the ligand is in excess.

In some embodiments, the β-diketonate (or other ligand) is provided in at least about a 4 molar excess compared to the salt of the at least one REE. In some embodiments, the β-diketonate (or other ligand) is provided in at least about a 6 molar excess compared to the salt of the at least one REE. In some embodiments, the β-diketonate is the diketonate of acetylacetone, the diketonate of 1,1,1,5,5,5-hexafluoroacetylacetone (hfac), the diketonate of 6,6,7,7,8,8-heptafluoro-2,2-dimethyl-3,5-oxtanedione (hfod); or the diketonate of 2,2,6,6-tetramethyl-3,5-heptanedione (hdpm).

In some embodiments, the β-diketonate or other ligand is provided in a solution with an organic solvent (e.g., an ether, such as diethyl ether, or an alcohol, such as ethanol). In some embodiments, the salt of the at least one REE is provided in an aqueous solution. The formed complex or complexes can be extracted into an organic solvent (e.g., ether) and dried.

In some embodiments, each complex volatizes at a temperature of about 250° C. or less. In some embodiments, each complex volatizes at a temperature between about 250° C. and about 175° C. In some embodiments, each complex volatizes at a temperature of about 225° C. or less or of about 200° C. or less. Thus, in some embodiments, the volatizing is performed at a temperature of about 250° C., about 225° C., or about 200° C. or less When a gas chromatography column is used, the contacting of step (d) can be performed under the flow of an inert or non-reactive gas. In some embodiments, the gas is helium. In some embodiments, the gas chromatography column is at a first temperature (e.g., about 45° C.) and the temperature is increased to a second temperature (e.g., about 220°) at a desired rate or rates.

The REE can be separated and/or recovered in some embodiments, with a purity of at least 99.999% or greater. In some embodiments, the purity can be 99.9999%. The recovery time for the REEs can be about 1 day or less (e.g., about 24, 23, 22, 21, 20, 19, 18, 17, 16, 15, 14, 13, 12, 11, 10, 9, or about 8 hours). Near 100% recovery rates from sample can be provided (e.g., about 80, 85, 90, 91, 92, 93, 94, 95, 96, 97, 98, 99, or about 100% recovery). The separation of one complex from another can be adjusted as necessary by choice of ligand (such as β-diketonate) and/or by changing one or more gas chromatography parameters (e.g., gas flow rate, column temperature, ramp rate or column size (diameter or length).

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Ln[Hfac]$_x$ Complexes

Ln[Hfac]$_x$ complexes were prepared in a manner similar to that described previously. See Berg and Acosta, Anal. Chim. Acta, Vol. 40, 101-113 (1968). See also Scheme 1, below.

Scheme 1. Synthesis of Lanthanide Hfac Complexes.

Dissolution:

Ligand Preparation:

Combination/Extraction:

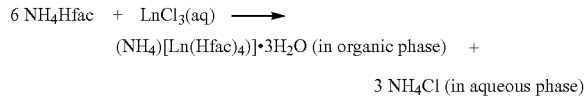

Rare earth oxides (e.g., SmCl$_3$, 99.99%, Sigma Aldrich, St Louis, Mo., United States of America) were combined with hot, concentrated HCl (ACS Reagent Grade, Fisher, Thermo Fisher Scientific, Waltham, Mass., United States of America) to yield the chloride salt in an acid solution. Hexafluoroacetylacetone (Acros Organics, Thermo Fisher Scientific, Waltham, Mass., United States of America) was obtained and combined with equimolar amounts of concentrated ammonium hydroxide (NH$_4$OH, Thermo Fisher Scientific, Waltham, Mass., United States of America) at 0° C. The two liquids reacted vigorously, producing HN$_4$Hfac as a white solid. The solid was stored in a desiccator until further use.

The NH$_4$Hfac was dissolved in 5 mL of diethyl ether (Et$_2$O, Thermo Fisher Scientific, Waltham, Mass., United States of America) to which aqueous SmCl$_3$ was added in a ratio of 4:1. The mixture was shaken vigorously for 30 seconds, and then allowed to sit for 5 minutes. This was repeated 3 times. At the conclusion of the last separation, the organic phase was drawn off and placed in a vacuum desiccator to dry the sample and remove the Et$_2$O. A solid residue remained after 24 hours of drying, resulting in Sm[Hfac]$_4$ (i.e., complex 1). Dy[Hfac]$_4$ (complex 2) and Tm[Hfac]$_4$ (complex 3) were prepared analogously. The yields for complex 1 and 3 were 35.0-36.3% and 57.2-59.2%, respectively.

Gas chromatography was performed using a Hewlett-Packard gas chromatography instrument (Hewlett-Packard, Palo Alto, Calif., United States of America) with an Agilent 6890 column and 5973 mass selective detector (Agilent Technologies, Santa Clara, Calif., United States of America). Helium was used as a carrier gas with a flow rate of 0.8 ml/min, on a 30 m column. The injection inlet was heated to 250° C. to volatize the samples. The oven temperature was set to 45° C., with a 2.00 min hold time. The oven was then heated at a rate of 5.0° C./min to a set point of 54° C. and held for 2.00 minutes, then the temperature was increased to 65° C. at a ramp rate of 5° C./min. Once at 65° C., the ramp rate was increased to 20° C./min and heated to 220° C. The average mass of (NH$_4$)$_3$.Ln[Hfac]$_6$.H$_2$O complexes was approximately 1300 amu, and since the 5973 mass selective detector has an upper limit of 600 amu for detection, the mass peak for the actual compounds is not observed.

Figure 5:
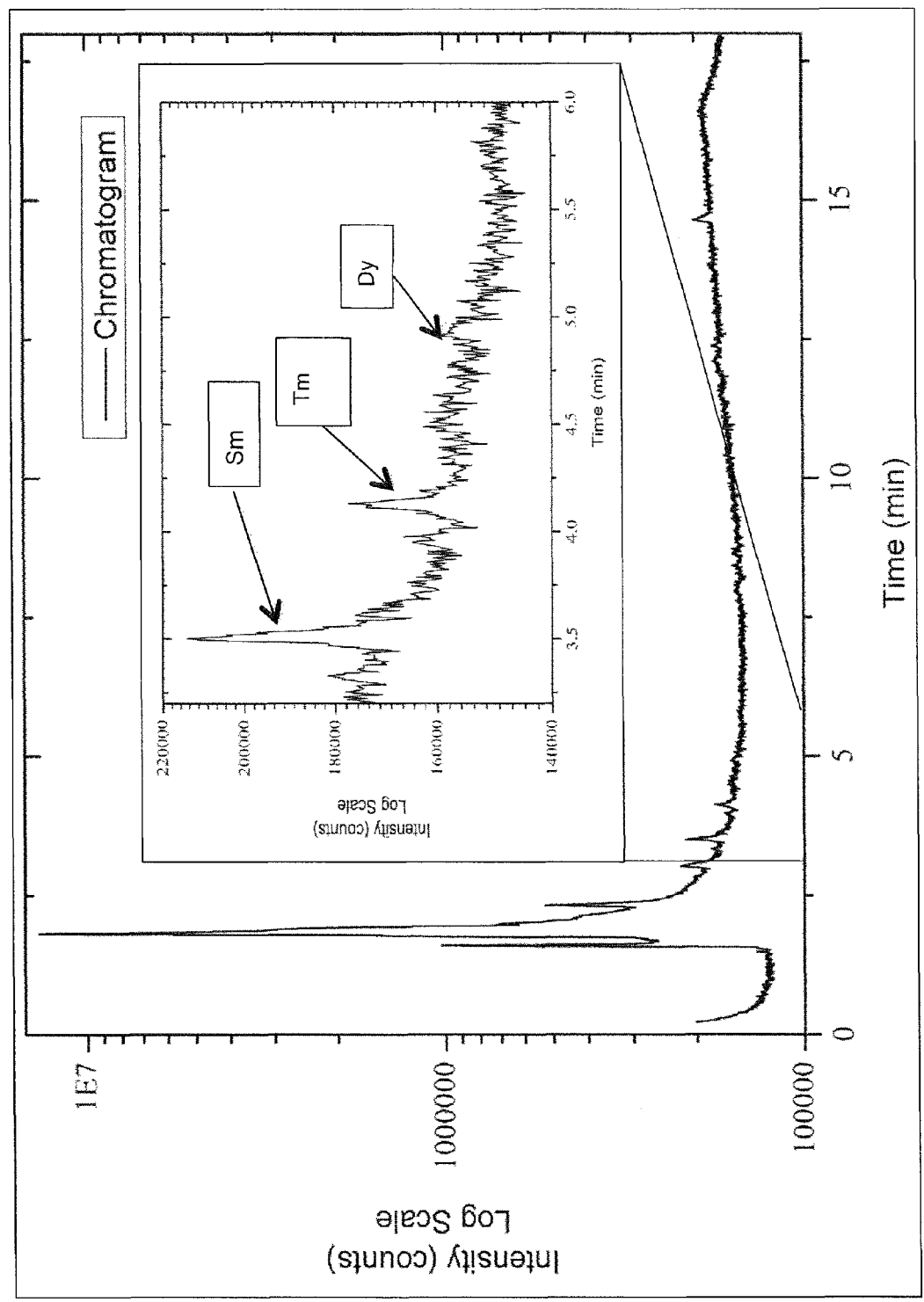
FIG. 5 is gas chromatogram of ethyl ether containing 0.1 gram per milliliter (g/mL) of a β-diketonate complex of samarium (Sm) and 1,1,1,5,5,5-hexafluoro-2,4-acetylacetonate (Hfac) (i.e., Sm[Hfac]$_4$, also referred to as complex 1); 0.1 g/mL of the β-diketonate complex of dysprosium (Dy) and Hfac (i.e., Dy[Hfac]$_4$, also referred to as complex 2); and 0.1 g/mL of the β-diketonate complex of thullium (Tm) and Hfac (i.e., Tm[Hfac]$_4$, also referred to as complex 3). The inset is a blown-up view of the chromatogram from about 2.9 minutes to 6 minutes. In the inset, the elution peak for complex 1 is indicated by the arrow from Sm, the peak for complex 3 is indicated by the arrow from Tm, and the peak for complex 2 is indicated by the arrow from Dy.
Figure 7:
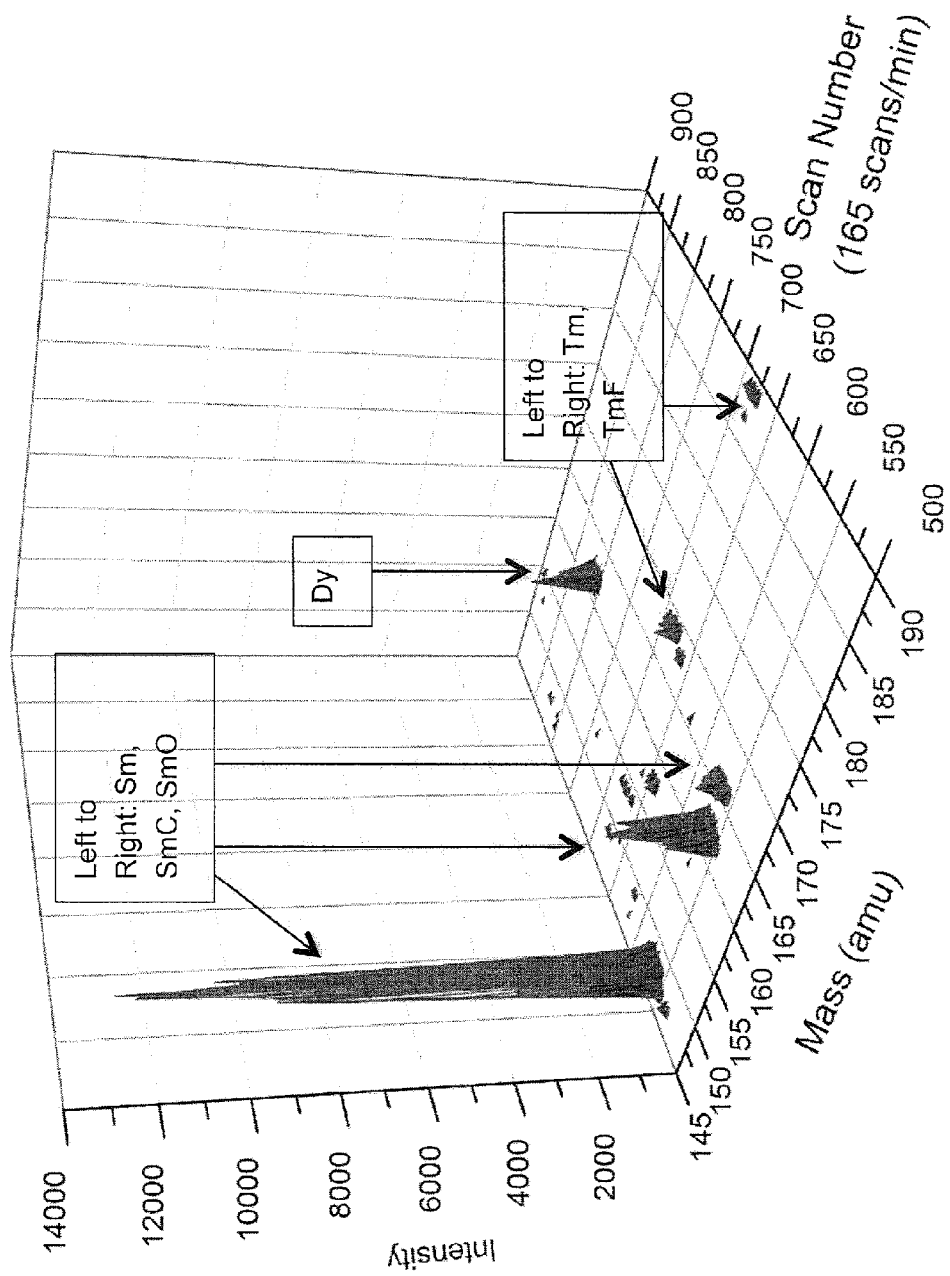
FIG. 7 is a separation profile of the gas chromatographic separation of complex 1, complex 2, and complex 3 described above for FIG. 5. The mass axis of the profile is restricted from 145 to 190 atomic mass units (amu). Complex 1 eluted at about 3.4-3.6 minutes, corresponding to scan number about 550 to about 575. The peaks marked Sm, SmC, and SmO relate to complex 1. Complex 2 eluted at 4.85-4.95 minutes, corresponding to scan number about 800 to about 825. The peak marked Dy relates to complex 2. Complex 3 eluted at 4.05-4.25 minutes, corresponding to scan number about 650 to about 700. The peaks marked Tm and TmF relate to complex 3.

The chromatographic results from the separation are presented in FIG. 5. As indicated in the chromatograph shown in FIG. 5, complex 1 eluted at 3.5 minutes, complex 2 at 4.9 minutes, and complex 3 at 4.15 minutes. The mass spectrum results that identify the peaks are shown in FIG. 7. The peaks that are presented in FIG. 5 represent the total ion flux response of the mass spectrometry detector to the sample as it is eluted from the column and not the mass-resolved response from the mass spectrum detector.

Figure 6:
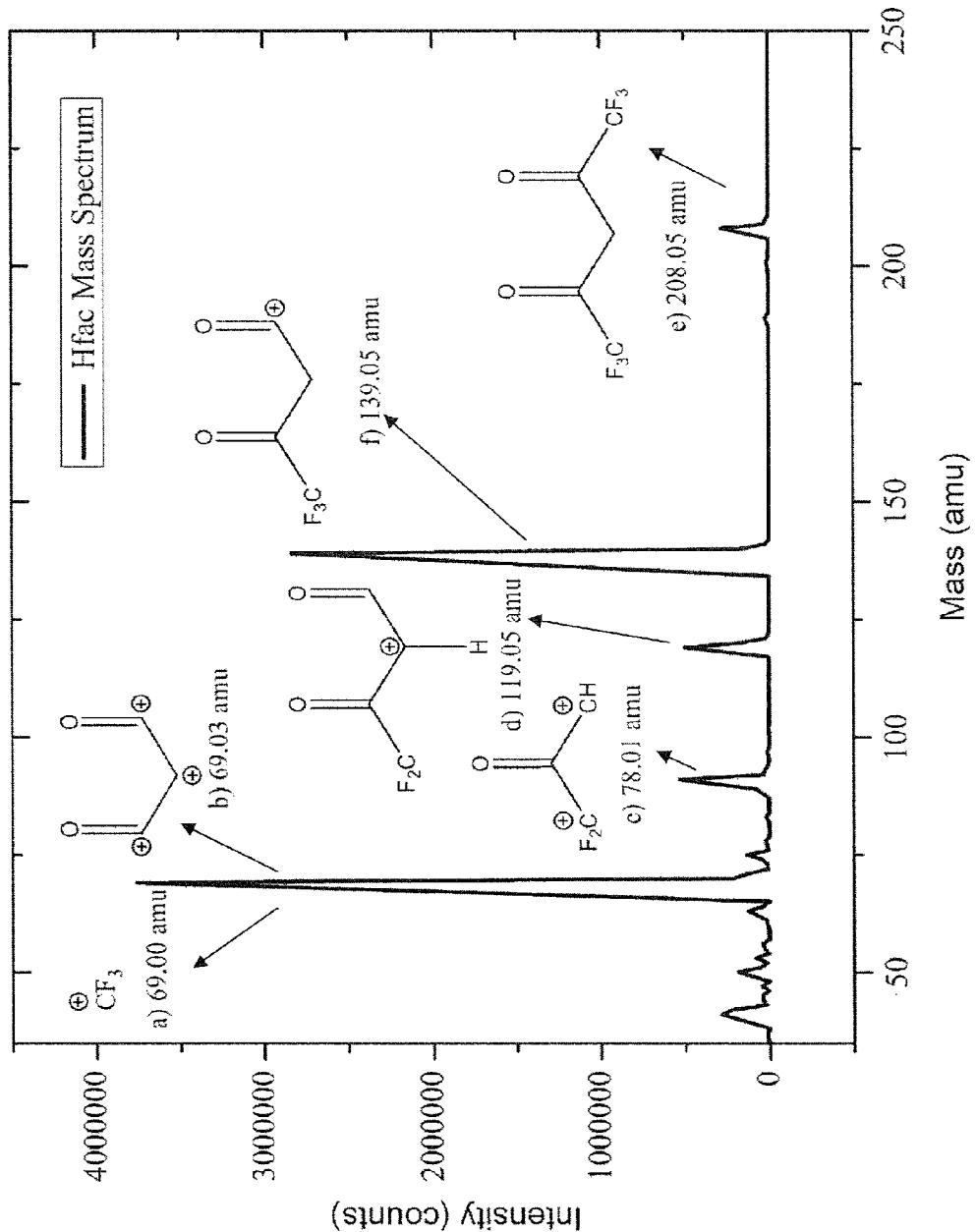
FIG. 6 is a mass spectrum of 1,1,1,5,5,5-hexafluoro-2,4-acetylacetonate (Hfac), showing the major decomposition fragments: (a) trifluoromethane (69.00 atomic mass units (amu)), (b) 1,3-propadione (69.03 amu), (c) 2,2-difluoromethyl-acetone (78.01 amu), (d) 4,4-difluoro-1,3-propadione (119.05 amu), (e) 1,1,1,5,5,5-hexafluoroacetylacetone (208.05 amu), and (f) 4,4,4-trifluoro-1,3-propadione (139.05 amu).

A blank sample containing only the solvent and the Hfac ligand was introduced into the mass spectrometer. The resulting mass fragments from Hfac are shown in FIG. 6. The most common fragment is that of trifluoromethane (69.00 amu), which is also heavily convoluted with the 1,3-propadione fragment (69.03 amu). The secondary 4,4, 4-trifluoro-1,3-propanedione fragment is observed at 139.05 amu. The full Hfac peak is observed at 208.05 amu, along with the 2,2-difluoromethyl-acetone fragment (78.01 amu) and 4,4-difluoro-1,3-propanedione fragment (119.05). Peaks below 69 amu are impurities on the column and solvent (CHCl$_3$) related peaks. The mass peak (119 amu) for chloroform is also convoluted with the 4,4-difluoro-1,3-propanedione fragment and is not distinguishable.

The separation profiles observed in FIG. 7 represent the response of the mass spectrum detector as a function of the number of scans taken. The total method time was approximately 14.8 minutes in length, and there were 2440 scans taken from the mass range of 1 to 500 amu. The response of the mass spectrum is similar to that of the flame ionization detector (FID) and the resulting separation times are as follows: Complex 1 is eluted at 3.4-3.6 minutes; complex 2 is eluted in a band at 4.85-4.95 minutes, and complex 3 is eluted at 4.05-4.25 minutes. FIG. 6 shows that there is good separation of the three compounds.

Without being bound to any one theory, it is believed that the separations of these complexes is largely based upon the interaction with the column and not the boiling or sublimation points, since the temperature of separations was well below the reported boiling or sublimation points of the compounds.

Resolution was calculated from the equation $\Delta t_r/w_{av}$, where $\Delta t_r$ is the difference in retention times between two peaks and $w_{av}$ is the average width at the base of the same two peaks. Resolution for the peaks of complex 1 and complex 3 was 3.25 and for complex 3 and complex 2 was 5.30. Any resolution greater than 1.5 is consider acceptable.

Example 2

Ln[Hfod]$_x$ Complexes

A series of Ln[Hfod]$_x$ complexes were synthesized from high-purity materials as shown in Scheme 2, below.

Scheme 2. Synthesis of Lanthanide Hfod Complexes.

Dissolution:

Ligand Preparation:

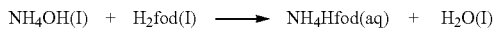

Combination/Extraction:

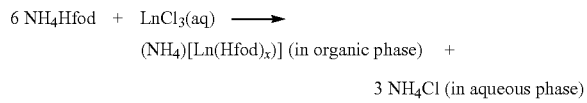

Rare earth oxides (99.99%, Sigma Aldrich, St Louis, Mo., United States of America) were combined with hot, concentrated HCl (ACS Reagent Grade, Fisher, Thermo Fisher Scientific, Waltham, Mass., United States of America) to yield the chloride salt in an acid solution. The solution was allowed to cool. 6,6,7,7,8,8,8-heptafluoro-2,2-dimethyl-3,5-octanedione (H[fod], 99.9%, Acros Organics, Thermo Fisher Scientific, Waltham, Mass., United States of America) was obtained and combined with equimolar amounts of concentrated NH$_4$OH (ACS Reagent Grade, Fisher, Thermo Fisher Scientific, Waltham, Mass., United States of America) at 0° C. The two liquids reacted vigorously and was stirred to fully react the reagents, producing ammonium Hfod (NH$_4$[Hfod]) as a white solid. The solid was then placed in a desiccator for storage.

Synthesis of the Ln[Hfod] complexes utilized a precipitation reaction. Previously synthesized and dried ammonium Hfod was dissolved in 5 mL of diether ether (ACS Reagent Grade, Fisher, Thermo Fisher Scientific, Waltham, Mass., United States of America). One millimole (mmol) of rare-earth chloride was dissolved into 50 mL of water and was then added to 4 mmol of dissolved NH$_4$[Hfod]. The solution was allowed to rest for at least 3 minutes, and then centrifuged and separated using a Büchner flask. The resultant material was dried under vacuum.

All reagents and solvents used in characterization were obtained from commercial sources and used without further purification. Elemental analysis was performed by Atlantic Microlab (Norcross, Ga., United States of America). Melting point analyses were performed using a Mettler Toledo MP50 melting point system (Mettler-Toledo International, Inc., Columbus, Ohio, United States of America) and four samples of each compound were measured simultaneously for good statistics. Infrared (IR) spectra were recorded using a Perkin Elmer Fourier transform-attenuated total reflectance-infrared (FT-ATR-IR) spectrometer spectrum 100 instrument (Perkin Elmer, Waltham, Mass., United States of America) in the range from 4000-550 cm$^{-1}$. Mass spectra were recorded using a GBC 9000 Opti-mass inductively coupled plasma time-of-flight mass spectrometer (ICP-TOF-MS, GBC Scientific Equipment, Braeside, Australia) for detection of the rare earth ions. NMR data for H and F were obtained using a Varian NMR system (Varian, Inc., Palo Alto, Calif., United States of America) at 500 MHz, using deuterated 1,4-dioxane (99%, Cambridge Isotopes Laboratories, Inc., Andover, Mass., United States of America) as a solvent.

Figure 8:
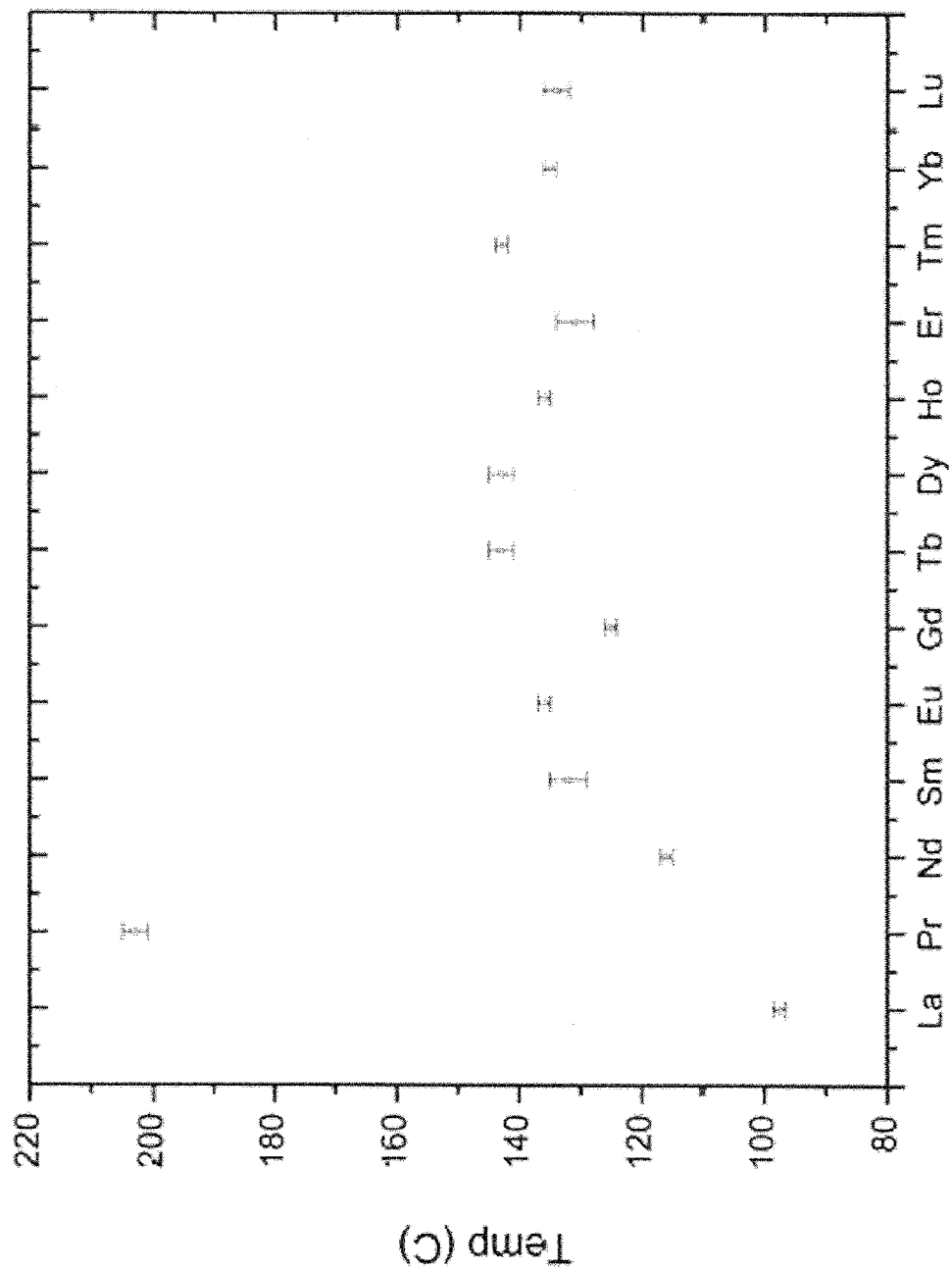
FIG. 8 is a graph showing the melting points of the β-diketonate complexes of the lanthanides where the β-diketonate is 6,6,7,7,8,8,8-heptafluoro-2,2-dimethyl-3,5-octanedione (Hfod).

The melting points of the Ln[Hfod]$_x$ samples are presented in FIG. 8. Previous reports for representative complexes have given the melting points for hydrated complex 4 (i.e., NH$_4${Sm(Hfod)$_4$}) to be 63-67° C. (anhydrous 208-218° C. with decomposition) for complex 5 (i.e., NH$_4${Nd(Hfod)$_4$}]) to be 210-215° C. (decoposition) and for hydrated complex 6 (i.e., NH$_4${Dy(Hfod)$_4$}]) to be 180-188° C. (anhydrous 103-107° C.). See Springer et al., Inorg. Chem., Vol. 6(6), 1105-1110 (1967).

The Shannon-Prewitt radii (see, e.g., Atwood, D. A., "The Rare Earth Elements: Fundamentals and Applications", John Wiley & Sons Ltd., 2012, p. 696) for the eight-coordinate lanthanide complexes do not correlate well and hence do not explain the distribution. While the melting points initially show a decrease for the light-lanthanides, the middle-lanthanides and heavy-lanthanides have similar regional trends.

The yields and elemental analysis for representative complexes 4 (i.e., NH$_4${Sm(Hfod)$_4$}) 5 (i.e., NH$_4${Nd(Hfod)$_4$}]) and 6 (i.e., NH$_4${Dy(Hfod)$_4$}]) are as follows: For 4. Yield 43.80%. Elemental analysis calc'd (%): C, 34.55; H, 3.32; N, 0.67; F, 38.03. Found: C, 33.42; H, 3.22; N, 0.63; F, 36.81. For 5: Yield 21.04%. Elemental analysis calc'd (%): C, 34.89; H, 3.37; N, 1.02; F, 38.02. Found: C, 34.87; H, 3.34; N, 1.02; F, 38.22; For 6: Yield: 14.34% Elemental analysis calc'd (%): C, 34.43; H, 3.32; N, 1.00; F, 38.13. Found: C, 34.67; H, 3.28; N, 1.03; F, 38.09.

Compound formulas were determined by minimizing the error between the calculated values and the data provided by Atlantic Microlab. Errors were generally 1-2%, with values higher than 4% being occasionally found on N and H. Without being bound to any one theory, this was attributed to slight residual impurities of NH$_4$ remaining within the synthesized complex.

The four-ligand complex was found for each of the rare earths presented. For 5, the sample was determined to be a mixture of both the three and four ligand complexes. The formula determination found water present in the sample mixtures. Two water molecules were consistently found without respect to the compound formula. Without being bound to any one theory, this can be attributed to the synthesis methodology or adsorption from the atmosphere. Only the tris complex has been previously reported, with speculation that the fod ligand might be too bulky to form a tetrakis complex. However, such complexes were found to form here.

NMR analysis. For NH$_4$[Hfod]: $^1$H NMR (C$_4$D$_8$O$_2$, 500 MHz) δ 6.17 (d, J=1.0 Hz, 1H), 1.38-1.26 (m, 11H), 0.10 (d, J=0.9 Hz, 1H. $^{13}$C NMR δ 203.83, 177.10, 116.61, 108.94, 107.10, 93.39, 39.59, 26.44. $^{19}$F NMR (C$_4$D$_8$O$_2$, 500 MHz) δ −80.61 (t, J=9.0 Hz), −121.69 (q, J=9.1 Hz), −126.94. For 4: $^1$H NMR (C$_4$D$_8$O$_2$, 500 MHz) δ 4.68 (s, 17H), 4.54 (tdd, J=8.8, 5.2, 3.5 Hz, 5H), 3.57 (solvent), 2.50 (s, 1H), 2.26 (dtd, J=9.8, 4.7, 4.1, 2.3 Hz, 9H). $^{19}$F NMR (C$_4$D$_8$O$_2$, 500 MHz) δ −80.47-80.87 (m, J=6.6 Hz), −119.62 (d, J=10.2 Hz), −125.60, −126.60 (d, J=4.4 Hz), −126.98. For 5: $^1$H NMR (C$_4$D$_8$O$_2$, 500 MHz) δ 5.17-5.11 (m, 1H), 4.97 (qd, J=7.0, 1.9 Hz, 6H), 2.70 (td, J=7.0, 1.8 Hz, 9H), 2.60 (s, 1H). $^{19}$F NMR (C$_4$D$_8$O$_2$, 500 MHz) δ −81.13 (d, J=38.8 Hz), −119.53, −126.93 (dd, J=261.5, 77.3 Hz). For 6: $^1$H NMR (C$_4$D$_8$O$_2$, 500 MHz) δ 11.35 (s, 1H), 4.03 (s, 10H), 1.73 (t, J=7.1 Hz, 3H). $^{19}$F NMR (C$_4$D$_8$O$_2$, 500 MHz) δ −68.13-82.92 (m), −116.78 (d, J=2312.9 Hz), −126.63 (d, J=275.8 Hz).

FTIR analysis. For 4: (ATR cm-1): 2974 (br), 1624 (m, sh), 1593 (w), 1458 (m, sh), 1396 (w), 1368 (m, sh), 1220 (sh), 1117 (sh), 1103 (m, sh), 1070 (m, sh), 797 (w), 755 (w), 741 (w), 687 (w). For 5: (ATR cm-1): 3353 (br), 2974 (br), 1624 (m, sh), 1593 (w), 1458 (m, sh), 1396 (w), 1368 (m, sh), 1220 (sh), 1117 (sh), 1070 (m, sh), 797 (w), 741 (w), 687 (w). For 6: (ATR cm-1): 2974 (br), 1624 (m, sh), 1593 (w), 1458 (m, sh), 1396 (w), 1368 (m, sh), 1220 (sh), 1117 (sh), 1103 (m, sh), 1070 (m, sh), 797 (w), 755 (w), 741 (w), 687 (w).

Functional groups such as the C—F stretches between 1178-1344 cm$^{-1}$ and 687-755 cm$^{-1}$ were indicative of the ligand's presence. Good correlation was found between the wavenumbers of the complexes from opposite ends of the lanthanide series. However, it is not clear where the distinction of metal-ligand wavenumbers can be resolved from the NH$_4$[Hfod] compound.

Figure 9:
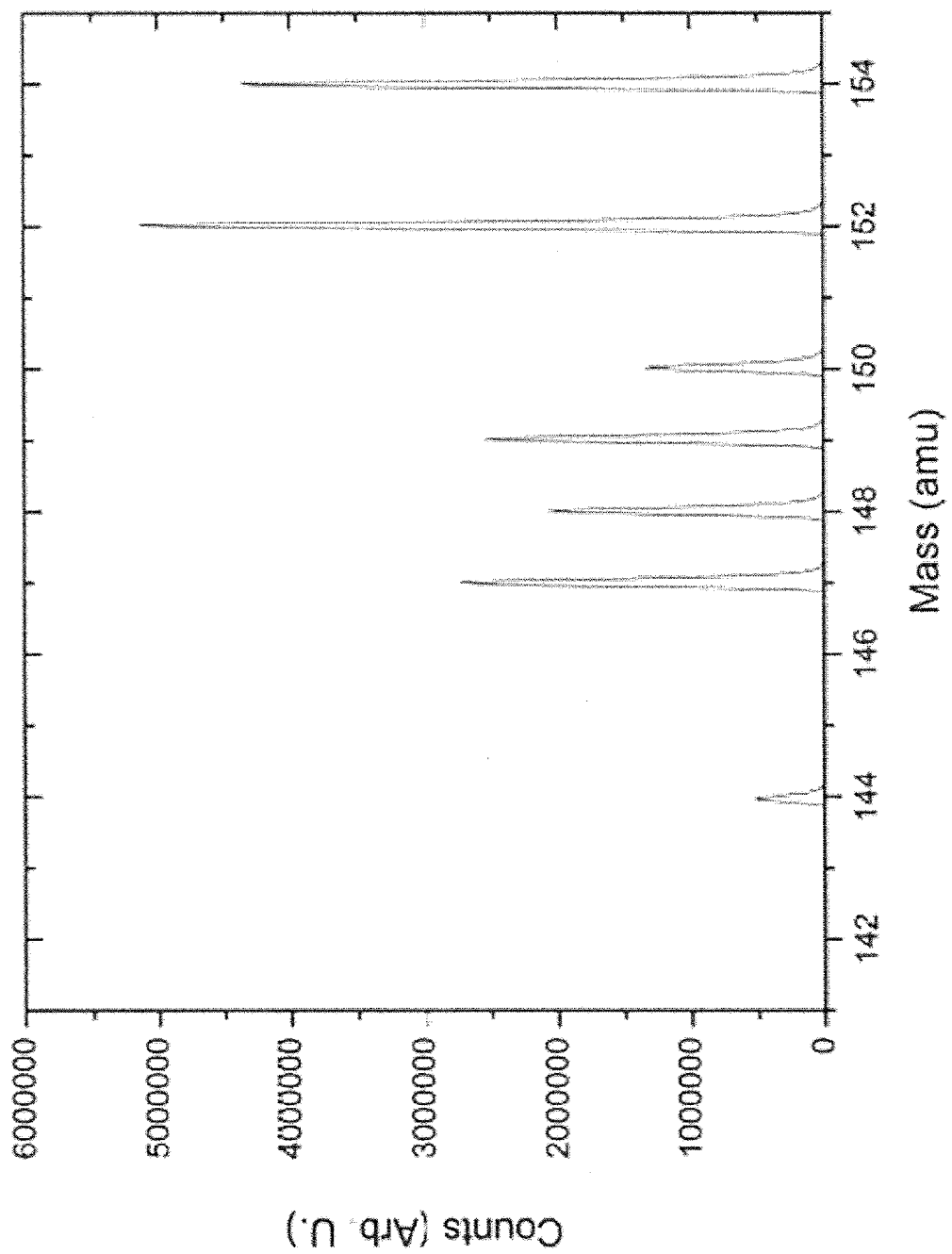
FIG. 9 is part of a mass spectrum of complex 4 (i.e., a β-diketonate complex of samarium (Sm) with the β-diketonate of 6,6,7,7,8,8,8-heptafluoro-2,2-dimethyl-3,5-octanedione (Hfod), i.e., [NH$_4$\{Sm(Hfod)$_4$\}]. The spectrum shows the peaks for various isotopes of Sm.
Figure 10:
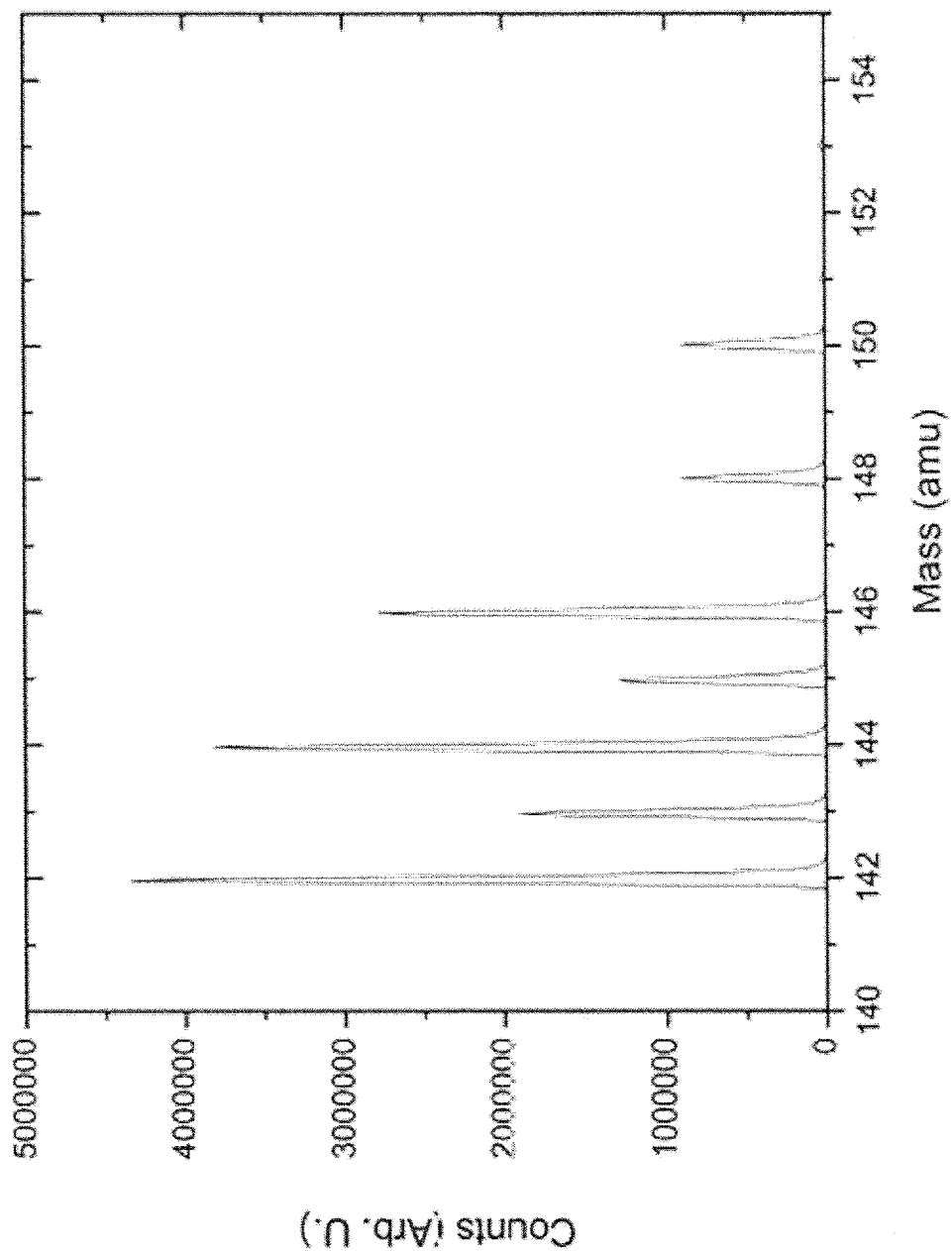
FIG. 10 is part of a mass spectrum of complex 5 (i.e., a β-diketonate complex of neodymium (Nd) with the β-diketonate of 6,6,7,7,8,8,8-heptafluoro-2,2-dimethyl-3,5-octanedione (Hfod), i.e., [NH$_4$\{Nd(Hfod)$_4$\}]. The spectrum shows the peaks for various isotopes of Nd.
Figure 11:
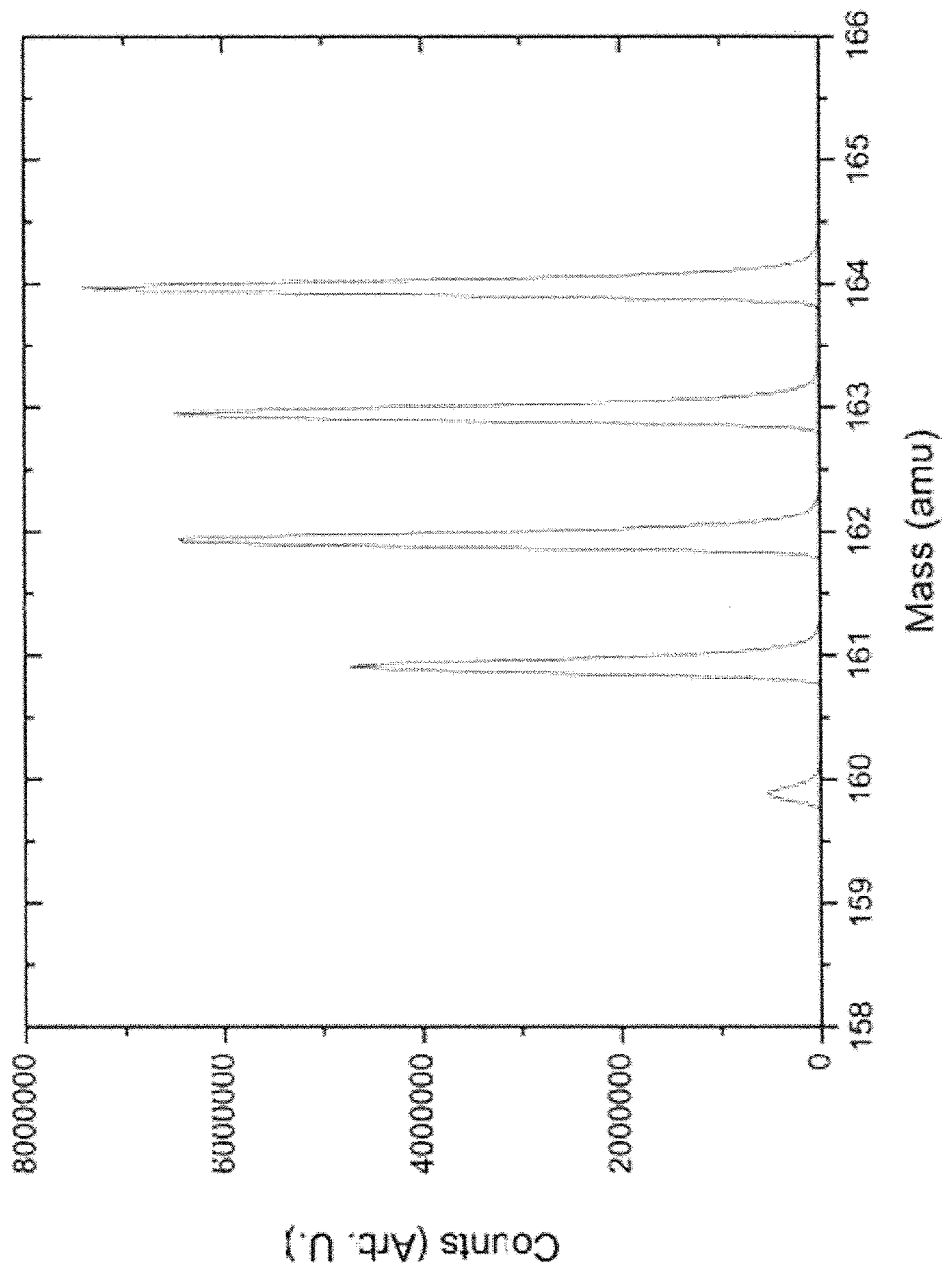
FIG. 11 is part of a mass spectrum of complex 6 (i.e., a β-diketonate complex of dysprosium (Dy) with the β-diketonate of 6,6,7,7,8,8,8-heptafluoro-2,2-dimethyl-3,5-octanedione (Hfod), i.e., [NH$_4$\{Dy(Hfod)$_4$\}]. The spectrum shows the peaks for various isotopes of Dy.

ICP-TOF-MS. Prepared samples of each of three rare earth complexes were analyzed with ICP-TOF-MS for rare earth metal content/isotopic ratios. The MS spectrum are shown in FIGS. 9-11. Complex 4 (FIG. 9) exhibits primary peaks at 144 amu (3.07% abundant), 147 amu (14.99% abundant), 148 amu (11.24% abundant), 149 amu (13.82% abundant), 150 amu (7.38% abundant), 152 amu (26.75% abundant), and 154 amu (22.75% abundant). Complex 5 (FIG. 10) demonstrates primary peaks at 142 amu (27.2% abundant), 143 amu (12.2% abundant), 144 amu (23.8% abundant), 145 amu (8.3% abundant), 146 amu (17.2% abundant), 148 amu (5.7% abundant), and 150 amu (5.6% abundant). Complex 6 (FIG. 11) shows primary peaks at 160 amu (2.34% abundant), 161 amu (18.91% abundant), 162 amu (25.52% abundant), 163 amu (24.90% abundant), and 164 amu (28.18% abundant). Peaks demonstrated in each of the three spectrum are in agreement with the natural isotopic abundance of the relevant REE.

Thus, in summary, three rare earth β-diketone complexes, 4 (i.e., NH$_4${Sm(Hfod)$_4$}) 5 (i.e., NH$_4${Nd(Hfod)$_4$}) and 6 (i.e., NH$_4${Dy(Hfod)$_4$}) were synthesized and characterized. Analysis verified the composition of the complexes. The IR and NMR data indicated that the Hfod ligands were forming M-O bonds with the central lanthanide atom.

Example 3

Additional Ln[Hfac] Complexes

Additional lanthanide complexes were prepared with the Hfac ligand as shown in Scheme 1 in Example 1, above, excepting that the resulting complexes were presumed to have the formulas (NH$_4$)$_3$[Ln(Hfac)$_6$].3H$_2$O. Yields for the La, Gd, and Lu complexes were 59.8%, 65.3% and 55.3% respectively. These complexes were analyzed via elemental analysis, IR and melting point determination as described in Example 2.

The melting points for the La, Gd, and Lu hfac complexes were 140-148° C., 173-184° C., and 217-221° C., respectively. Elemental analysis was as follows: For the La complex; Elemental analysis calc'd (%): C, 25.16; H, 1.06; N, 2.93; F, 47.7.5 Found: C, 224.7; H, 1.31; N, 2.65; F, 43.41. For the Gd complex; Elemental analysis calc'd (%): C, 24.84; H, 1.04; N, 2.9; F, 47.15. Found: C, 24.35; H, 0.96; N, 2.95; F, 42.74, For the Lu complex: Elemental analysis calc'd (%): C, 24.13; H, 0.89; N, 2.25; F, 45.81. Found: C, 23.62; H, 0.78; N, 1.63; F, 42.09. Without being bound to any one theory, it is believed that the differences in F % can be due to possible residual NH$_4$Hfac, while hydration differences can be responsible for differences in hydrogen amounts.

X-ray diffraction studies indicated increasing crystallinity as one moves across the Ln series. Both NH$_4$Hfac and the Lu complex have an orthorhombic unit crystal system.

Major peaks from the FT-ATR-IR spectra for NH4Hfac and for the La, Gd, and Lu complexes are summarized in Table 1, together with the functional assignments for the peaks. In Table 1, the wavelengths for the peaks are provided in cm$^{-1}$.

TABLE 1

IR Results for Additional Hfac Complexes.

| NH$_3$Hfac | La Complex | Gd Complex | Lu Complex | Functional Assignment |
|---|---|---|---|---|
| 738 | 737 | 744 | 738 | C—CF$_3$ stretch |
| 799 | 806 | 804 | 821 | C—H out of plane bend |
| 1113 | 1130 | 1136 | 1115 | C—H in-plane bend |
| 1176 | 1187 | | 1177 | C—F stretch |
| 1203 | 1203 | 1202 | 1204 | C—F stretch |
| 1271 | 1270 | 1253 | 1271 | C—F stretch |
| 1455 | 1458 | 1472 | 1456 | C—H bend, [Hfac]-metal coordination |
| | 1537 | 1537 | 1536 | C—O stretch, C—H bend, [Hfac]-metal coordination |
| | 1563 | 1563 | 1562 | C=C stretch, [Hfac]-metal coordination |
| 1656 | 1645 | 1645 | 1652 | C—O stretch, [Hfac]-metal coordination |
| 3260 | 3332 | 3040 | 3253 | O—H stretch |

Example 4

Ln[hdpm]$_x$ Complexes

A series of Ln[hdpm]$_x$ complexes were synthesized from high-purity materials as shown in Scheme 3, below.

Scheme 3. Synthesis of Lanthanide hdpm Complexes.

Dissolution:

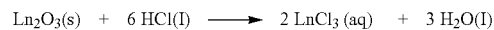

Ln$_2$O$_3$(s) + 6 HCl(l) ⟶ 2 LnCl$_3$ (aq) + 3 H$_2$O(l)

Ligand Preparation:

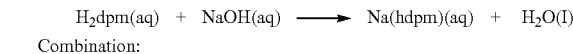

H$_2$dpm(aq) + NaOH(aq) ⟶ Na(hdpm)(aq) + H$_2$O(l)

Combination:

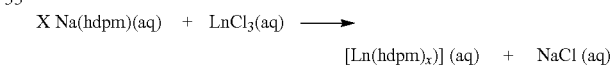

X Na(hdpm)(aq) + LnCl$_3$(aq) ⟶ [Ln(hdpm)$_x$)] (aq) + NaCl (aq)

The sodium diketonate hpdm was prepared as shown in the ligand preparation step of Scheme 3. Hdpm was dissolved in aqueous sodium hydroxide comprising 50% ethanol and stirred under an argon atmosphere. Then an excess of the sodium diketonate was mixed with the lanthanide salt in an aqueous solution containing 50% ethanol at 500 torr under argon and stirred. Yields for these complexes are shown in Table 2.

TABLE 2

Yields for Synthesis of hdpm Complexes of Rare Earth Elements.

| Rare Earth Element | % Yield |
|---|---|
| La | 73.2 |
| Nd | 60.3 |
| Eu | 52.4 |
| Gd | 54.8 |
| Ho | 57.3 |
| Er | 52.3 |
| Tm | 47.4 |
| Yb | 58.3 |

Figure 12:
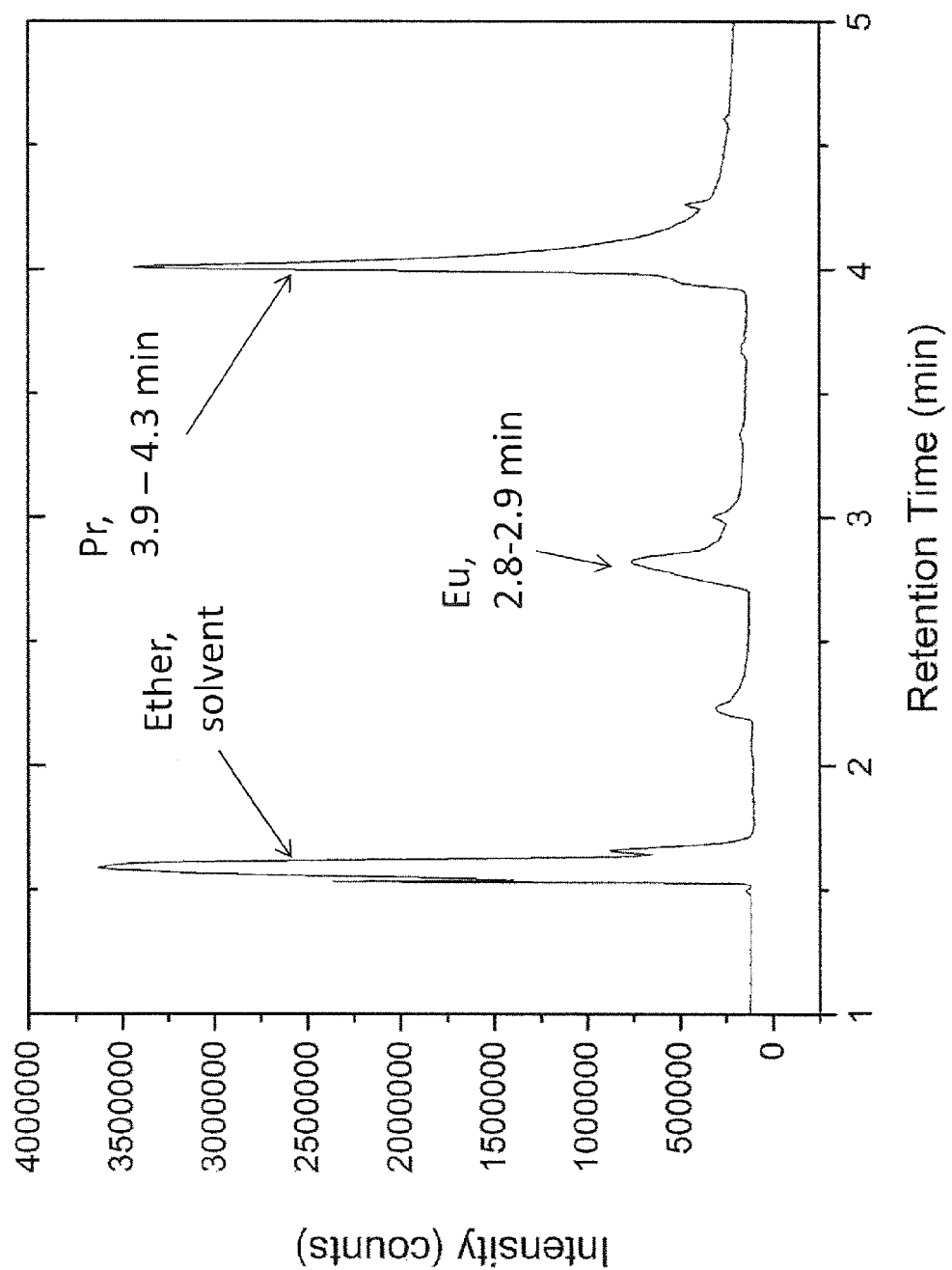
FIG. 12 is gas chromatogram of ethyl ether (Ether, solvent) containing a β-diketonate complex of europium (Eu) and 2,2,6,6-tetramethyl-3,5-heptanedione (Hdpm) and a β-diketonate complex of praseodymium (Pr) and Hdpm. The Eu complex eluted at 2.8-2.9 minutes and the Pr complex eluted at 3.9-4.3 minutes.
Figure 13:
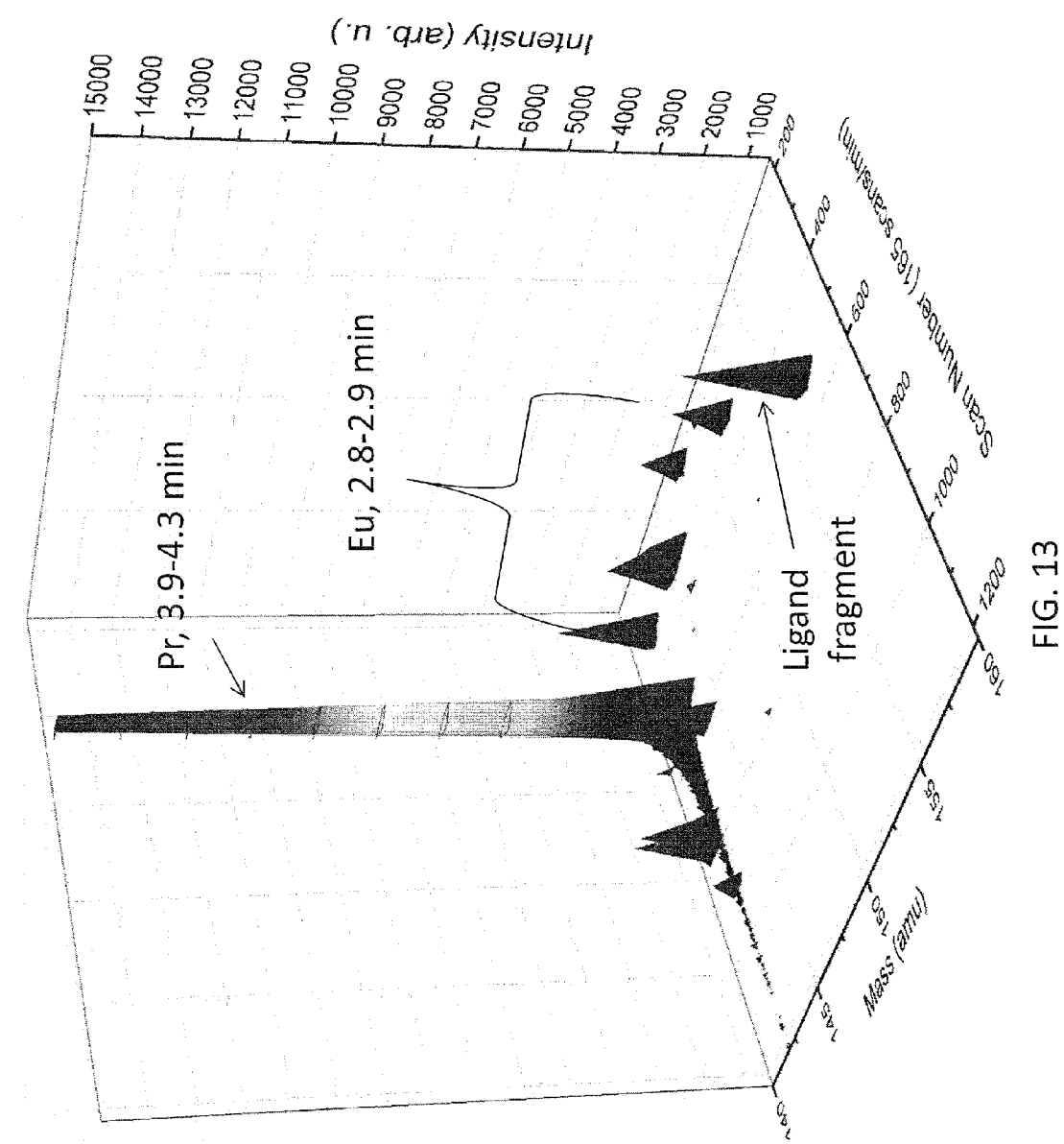
FIG. 13 is a separation profile of the gas chromatographic separation the europium (Eu) and praseodymium (Pr) β-diketonate complexes described for FIG. 12. The mass axis of the profile is restricted from 140 to 160 atomic mass units (amu).

FIGS. 12 and 13 show the separation of the Eu and Pr hdpm complexes via gas chromatography. The resolution of the Pr and Eu complexes was 7.43.

Example 5

Thermodynamic Analysis

The thermodynamic parameters (e.g., the Gibbs free energy of sublimation ($\Delta G_{subl}$), entropy of sublimation ($\Delta S_{subl}$), enthalpy of sublimation ($\Delta H_{subl}$) for various β-diketonate complexes were measured and used to calculate approximate predicted retention times. Thermogravemetric analysis (TGA) was performed on a Perkin Elmer Pyris 1 TGA (Perkin Elmer, Waltham, Mass., United States of America). Samples were run under nitrogen, held at 105° C. for 5 minutes or until signal equilibrated within 0.005° C., heated from 105° C.-350° C. at 10°/min, then held at 350° for two additional minutes. The differential thermal analysis (DTA) (or differential scanning calorimetry (DSC)) curve was found via numerical differentiation of the raw TGA data.

The TGA/DSC data collected was analyzed by three previously reported methods, i.e., that of Freeman and Carroll, Horowitz-Metzger, and Coats-Redfern. See Freeman and Carroll, J. Phys. Chem., Vol. 73, No. 3, 5-6 (1969); Horowitz and Metzger, Anal. Chem., Vol. 35 (10), 1464-1468 (1963); and Coats and Redfern, Polm Lett., Vol. 3, 917-920 (1965). The results from the TGA/DSC methods are presented in Table 3. The ionic radius of the relevant chemical element is given in angstroms, the Ts is the temperature of sublimation, the range is the region of change (in K), the $\Delta E$ is the energy of activation for the process (in J), the A or Z factor is a correction factor corresponds the method used to analyze the compound. Comp refers to Complex, Meth refers to method, HM corresponds to the Horowitz-Metzger, CR corresponds to the Coats-Redfern method, and FC corresponds to the Freeman-Carroll method.

TABLE 3

The complete thermodynamic parameters for the Ln[hfac], Ln[hfod], and Ln[hdpm] compounds.

| Ionic Rad. (ang) | Comp | Meth | Ts (K) | Range (K) | n | ΔE | A or Z | ΔS | ΔH | ΔG |
|---|---|---|---|---|---|---|---|---|---|---|
| 91.2 | Dy hfac | CR | 504.01 | 471.3-509.17 | 0.227 | 90.133 | 1.687E+07 | −0.1109 | 85.94 | 141.85 |
| 91.2 | Dy hfac | HM | | | | 104.08 | 5.022E+08 | −0.0827 | 99.89 | 141.58 |
| 91.2 | Dy hfac | FC | | | | 84.183 | 3.659E+06 | −0.1236 | 79.99 | 142.31 |
| 91.2 | Dy hfod | CR | 500 | 466.15-505.04 | 0.468 | 104.39 | 7.271E+08 | −0.0796 | 100.23 | 140.01 |
| 91.2 | Dy hfod | HM | | | | 119.4 | 2.845E+10 | −0.0491 | 115.24 | 139.78 |
| 91.2 | Dy hfod | FC | | | | 115.86 | 1.225E+10 | −0.0561 | 111.71 | 139.75 |
| 89 | Er hfac | CR | 484.3 | 450.8-489.32 | 0.411 | 70.785 | 2.849E+05 | −0.1445 | 66.76 | 136.75 |
| 89 | Er hfac | HM | | | | 83.67 | 7.559E+06 | −0.1173 | 79.64 | 136.44 |
| 89 | Er hfac | FC | | | | 109.55 | 5.546E+09 | −0.0624 | 105.53 | 135.75 |
| 94.7 | Eu hdpm | CR | 556.95 | 524.05-562 | 0.965 | 103.09 | 3.401E+07 | −0.1059 | 98.46 | 157.46 |
| 94.7 | Eu hdpm | HM | | | | 118.05 | 8.989E+08 | −0.0787 | 113.42 | 157.25 |
| 94.7 | Eu hdpm | FC | | | | 108.48 | 1.111E+08 | −0.0961 | 103.85 | 157.37 |
| 94.7 | Eu hfac | CR | 488.05 | 455.15-493.19 | 0.323 | 67.401 | 9.955E+04 | −0.1533 | 63.34 | 138.18 |
| 94.7 | Eu hfac | HM | | | | 80.128 | 2.538E+06 | −0.1264 | 76.07 | 137.76 |
| 94.7 | Eu hfac | FC | | | | 136.9 | 4.008E+12 | −0.0077 | 132.84 | 136.62 |
| 93.8 | Gd hfac | CR | 488 | 455.02-493.09 | 0.248 | 34.857 | 1.965E+01 | −0.2243 | 30.80 | 140.24 |
| 93.8 | Gd hfac | HM | | | | 45.582 | 2.903E+02 | −0.2019 | 41.53 | 140.04 |
| 93.8 | Gd hfac | FC | | | | 142.95 | 1.279E+13 | 0.0019 | 138.89 | 137.96 |
| 90.1 | Ho hdpm | CR | 512.22 | 478.95-517.49 | 0.471 | 100.64 | 1.517E+08 | −0.0928 | 96.38 | 143.92 |
| 90.1 | Ho hdpm | HM | | | | 115.3 | 5.038E+09 | −0.0637 | 111.04 | 143.65 |
| 90.1 | Ho hdpm | FC | | | | 110.22 | 1.541E+09 | −0.0735 | 105.96 | 143.62 |
| 90.1 | Ho hfac | CR | 479.99 | 449.07-484.8 | 0.604 | 113.45 | 2.362E+10 | −0.0503 | 109.46 | 133.59 |
| 90.1 | Ho hfac | HM | | | | 128.23 | 1.004E+12 | −0.0191 | 124.24 | 133.41 |
| 90.1 | Ho hfac | FC | | | | 119.5 | 1.130E+11 | −0.0373 | 115.51 | 133.4 |
| 103 | La hfac | CR | 474.09 | 441.77-478.99 | 1.736 | 41.849 | 1.769E+02 | −0.2058 | 37.91 | 135.45 |
| 103 | La hfac | HM | | | | 52.876 | 3.157E+03 | −0.1818 | 48.93 | 135.12 |
| 103 | La hfac | FC | | | | 122.52 | 2.417E+11 | −0.0309 | 118.58 | 133.2 |
| 103 | La hfod | CR | 553.18 | 519.45-558.84 | 0.132 | 90.708 | 2.371E+06 | −0.1280 | 86.11 | 156.93 |
| 103 | La hfod | HM | | | | 105.08 | 5.749E+07 | −0.1015 | 100.48 | 156.63 |
| 103 | La hfod | FC | | | | 32.025 | 3.870E+00 | −0.2388 | 27.43 | 159.53 |
| 86.1 | Lu hfac | CR | 515.55 | 482.45-520.67 | 0.470 | 115.96 | 5.280E+09 | −0.0633 | 111.67 | 144.33 |
| 86.1 | Lu hfac | HM | | | | 131.53 | 2.100E+11 | −0.0327 | 127.24 | 144.11 |
| 86.1 | Lu hfac | FC | | | | 120.39 | 1.511E+10 | −0.0546 | 116.10 | 144.25 |
| 98.3 | Nd hfac | CR | 477.48 | 445.12-482.55 | 0.467 | 22.088 | 7.535E−01 | −0.2512 | 18.12 | 138.06 |
| 98.3 | Nd hfac | HM | | | | 31.834 | 8.501E+00 | −0.2311 | 27.86 | 138.18 |
| 98.3 | Nd hfac | FC | | | | 140.88 | 1.344E+13 | 0.0025 | 136.91 | 135.72 |
| 98.3 | Nd hfod | CR | 560.24 | 527.39-565.47 | 0.915 | 121.15 | 1.538E+09 | −0.0743 | 116.49 | 158.11 |
| 98.3 | Nd hfod | HM | | | | 137.4 | 5.667E+10 | −0.0443 | 132.74 | 157.56 |
| 98.3 | Nd hfod | FC | | | | 198.88 | 3.881E+16 | 0.0674 | 194.22 | 156.45 |
| 99 | Pr hdpm | CR | 539.07 | 504.58-544.18 | 0.529 | 122.71 | 7.334E+09 | −0.0610 | 118.23 | 151.1 |

TABLE 3-continued

The complete thermodynamic parameters for the Ln[hfac], Ln[hfod], and Ln[hdpm] compounds.

| Ionic Rad. (ang) | Comp | Meth | Ts (K) | Range (K) | n | ΔE | A or Z | ΔS | ΔH | ΔG |
|---|---|---|---|---|---|---|---|---|---|---|
| 99 | Pr hdpm | HM | | | | 138.8 | 2.690E+11 | −0.0310 | 134.31 | 151.04 |
| 99 | Pr hdpm | FC | | | | 101.28 | 5.319E+07 | −0.1019 | 96.80 | 151.75 |
| 99 | Pr hfac | CR | 476.52 | 444.52-481.55 | 1.914 | 74.508 | 9.478E+05 | −0.1344 | 70.55 | 134.59 |
| 99 | Pr hfac | HM | | | | 87.778 | 3.243E+07 | −0.1050 | 83.82 | 133.86 |
| 99 | Pr hfac | FC | | | | 198.67 | 8.099E+19 | 0.1323 | 194.71 | 131.66 |
| 95.8 | Sm hfac | CR | 464.97 | 434.33-469.69 | 0.432 | 23.961 | 1.528E+00 | −0.2451 | 20.10 | 134.06 |
| 95.8 | Sm hfac | HM | | | | 33.579 | 1.842E+01 | −0.2244 | 29.71 | 134.05 |
| 95.8 | Sm hfac | FC | | | | 157.94 | 3.353E+15 | 0.0486 | 154.07 | 131.47 |
| 95.8 | Sm hfod | CR | 551.21 | 517.99-556.39 | 0.191 | 86.815 | 1.047E+06 | −0.1348 | 82.23 | 156.53 |
| 95.8 | Sm hfod | HM | | | | 101.04 | 2.503E+07 | −0.1084 | 96.46 | 156.2 |
| 95.8 | Sm hfod | FC | | | | 111.79 | 2.531E+08 | −0.0892 | 107.21 | 156.35 |
| 88 | Tm hdpm | CR | 524.41 | 491.39-529.45 | 0.676 | 73.159 | 1.154E+05 | −0.1527 | 68.80 | 148.88 |
| 88 | Tm hdpm | HM | | | | 86.332 | 2.500E+06 | −0.1271 | 81.97 | 148.64 |
| 88 | Tm hdpm | FC | | | | 92.764 | 1.141E+07 | −0.1145 | 88.40 | 148.45 |

Figure 14:
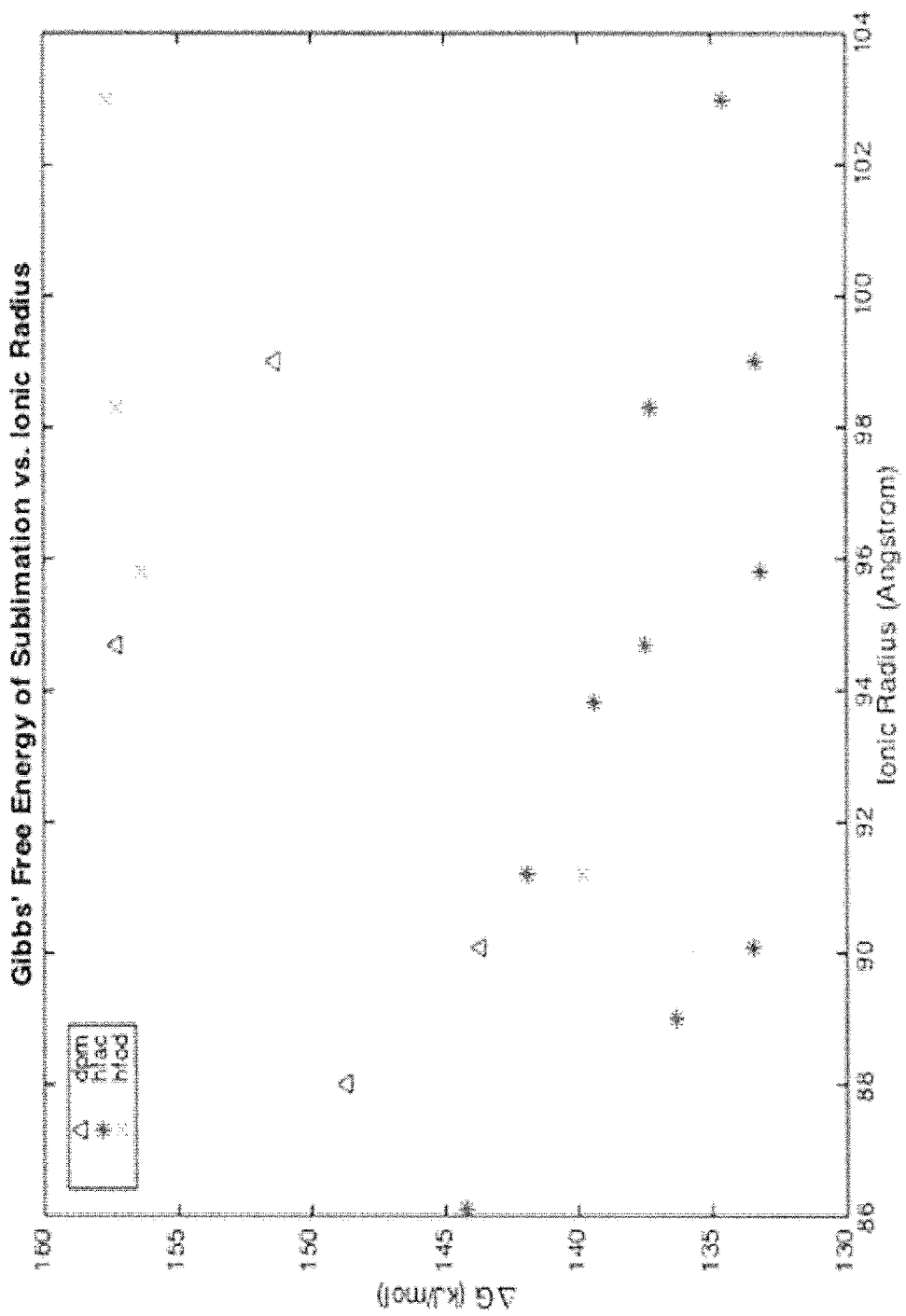
FIG. 14 is a graph of the Gibbs free energy (ΔG) of sublimation (in kiloJoules per mole (kJ/mol)) of various β-diketonate complexes of rare earth elements versus the ionic radius (in angstroms) of the rare earth element in the complex. Data is provided for complexes where the β-diketonate is the β-diketonate of 2,2,6,6-tetramethyl-3,5-heptanedione (hdpm or dpm, open triangles); 1,1,1,5,5,5-hexafluoro-2,4-acetylacetonate (hfac,*); and the β-diketonate of 6,6,7,7,8,8,8-heptafluoro-2,2-dimethyl-3,5-octanedione (hfod, x). The Gibbs free energy of sublimation values are the averages of the values calculated from thermogravimetric analysis/differential scanning calorimetry (TGA/DSC) using the Horowitz-Metzger method and the Coats-Redferm method.

The some of the results of from Table 3 are shown graphically in FIG. 14, where the average (of the HM and CR methods) Gibbs' free energy of sublimation (abscissa) is plotted as a function of the ionic radius of the metal compounds. The Ln[hfac] compounds trend towards lower values of ΔG, while the Ln[hfod] compounds trend towards larger values as the ionic radius increases. The Ln[hdpm] compounds do not have an apparent trend as a function of atomic radius.

The thermodynamic data was used to predict retention times for thermochromatography as described by Eichler et al. See Eichler et al., "Thermochemical Data from Gas Phase Adsorption and Methods of Their Estimation" in The Chemistry of Superheavy Elements, Springer Berlin Heidelberg, pp. 375-413 (2014). The predicted retention time, $t_r$, was calculated using Equation 1.

$$t_r = \frac{LT_0\phi}{\bar{V}_0 T_{iso}} * \left(1 + \frac{s}{v} * \frac{V}{100A} * \exp\left(-\frac{\Delta H^0_{ads}}{RT_{iso}}\right) * \exp\left(\frac{\Delta S^0_{ads}}{R}\right)\right) \quad (1)$$

where L is the length of the column, $T_0$ is standard temperature 298.15 K, $\phi$ is the free open cross-sectional area of the column, $\bar{V}_0$ is the carrier gas flow at standard temperature and pressure (STP), $T_{iso}$ is the isothermal column temperature, s is the open surface of column per 1 m column length, v is the open volume of the column per 1 m column length, V is the inner volume of the column, A is the inner surface per 1 m of column length, and R is the ideal gas constant. The enthalpy of adsorption, $\Delta H°_{ads}$, was determined using Equation 2.

$$-\Delta H^0_{ads} = (2.9 \pm 16) + (0.73 \pm 0.1) * \Delta H^0_{subl} \quad (2)$$

where the enthalpy of sublimation was taken from the thermodynamic models mentioned previously. The Coats-Redfern and the Horowitz-Metzger methods were used for calculation of the parameter, while the Freeman-Carroll was not used due to the inconsistent nature of parameter values obtained from that method. The calculation of the entropy of adsorption, $\Delta S°_{ads}$, was calculated using Equation 3.

$$\Delta S^0_{ads} = R\left(\ln\left(\frac{100A}{V * v_b}\right) * \sqrt{\frac{R * T}{2 * \pi * M_a}} + \frac{1}{2}\right) \quad (3)$$

where the entropy of adsorption is related to R, the ideal gas constant, the area of the column, A, the volume of the column, V, the phonon frequency, vb, the temperature, T, and the mass of the adsorbing material, $M_a$. The approximate retention times using a thermochromatography unit fitted with a 30 m $SiO_2$ column operating at 150° C., with a flow rate of 0.8 cm/s and an inner diameter of 0.5 mm, were approximated and tabulated in Table 4.

TABLE 4

The calculated retention times for selected Ln[hfac], Ln[hfod], and Ln[hdpm] compounds

| | Ho[hdpm] | La[hfod] | Lu[hfac] |
|---|---|---|---|
| MW (g/mol) | 734.37 | 1045.47 | 1025.24 |
| $\Delta H_{subl}$ (kJ/mol) | 103.7 | 93.3 | 119.5 |
| $\Delta H_{ads}$ (kJ/mol) | −78.6 | −71.0 | −90.1 |
| $\Delta S_{ads}$ (kJ/mol-K) | −0.142 | −0.119 | −0.120 |
| $t_r$ (s) | 1.496E+05 | 2.965E+05 | 5.789E+07 |

As indicated in Table 4, the thermodynamic predictions indicate that the thermochromatographic separation of β-diketonate complexes of rare earth elements would require long separation times. However, in the present studies, the observed separation times are much shorter. See e.g., Examples 1 and 4 and Table 5, below. Without being bound to any one theory, this discrepancy could be the result of the approximations used for a variety of the theoretical parameters of the model and the differences in chemistry between the lanthanide β-diketonates and the super heavy elements upon which the model was based. It is possible that the calculated retention time values can be improved by finding better approximations for some of the values used (e.g., the enthalpy and entropy of adsorption).

TABLE 5

Comparison of Observed and Calculated Retention Times for β-Diketonate Complexes of Rare Earth Elements.

| β-diketonate | Average Observed Retention Time (sec) | Calculated Retention Time (sec) |
|---|---|---|
| hfac | 2.25 × 10² | 5.78 × 10⁷ |
| hfod | 1.53 × 10² | 2.96 × 10⁵ |
| hdpm | 2.07 × 10² | 1.49 × 10⁵ |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of separating a mixture comprising atoms of at least two chemical elements, wherein each of said at least two chemical elements is selected from the group consisting of a rare earth element, uranium (U), thorium (Th), an actinide, and a heavy transition metal; the method comprising:
    (a) providing a sample comprising a compound or compounds comprising atoms of at least two of said chemical elements;
    (b) forming a mixture comprising a complex of each of the at least two chemical elements, wherein each complex comprises one of the at least two chemical elements and a ligand, further wherein the mixture comprises a tetrakis complex of each of the at least two chemical elements and the ligand, and wherein the mixture is formed by (i) contacting the sample with a strong acid to form a mixture of salts, wherein the mixture of salts comprises a salt of each of the at least two chemical elements, and (ii) contacting the mixture of salts with an at least four molar excess of the ligand as compared to the salts; and
    (c) volatizing the complexes of the mixture of step (b), thereby separating the complexes.

2. The method of claim 1, wherein step (c) comprises heating the mixture slowly to separate the mixture based on differences in volatization temperature.

3. The method of claim 1, wherein step (c) comprises heating the mixture to a predetermined temperature to volatize each of the complexes in the mixture and applying the volatized mixture to a gas chromatography column.

4. The method of claim 1, wherein the ligand is selected from the group consisting of a ketone, an enolate, a polyketone, a polyketonate, a β-diketonate, an ether, a polyether, and a polyalcohol.

5. The method of claim 1, wherein the sample comprises an oxide of each of the at least two chemical elements.

6. The method of claim 1, wherein each of the at least two chemical elements is a rare earth element selected from the group consisting of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

7. The method of claim 1, wherein the sample is a sample comprising nuclear fission and/or activation products or is a sample comprising waste from electronic and/or high technology products.

8. The method of claim 1, wherein the strong acid comprises hydrochloric acid and the mixture of salts comprises a mixture of hydrochloride salts.

9. The method of claim 8, wherein the strong acid further comprises one or more of nitric acid, hydrofluoric acid, and sulfuric acid.

10. The method of claim 1, wherein the ligand is a β-diketonate and the β-diketonate is provided as an ammonium salt.

11. The method of claim 1, wherein the ligand is a β-diketonate selected from the group consisting of the diketonate of acetylacetone, the diketonate of 1,1,1,5,5,5-hexafluoroacetylacetone (hfac), the diketonate of 6,6,7,7,8,8-heptafluoro-2,2-dimethyl-3,5-octanedione (hfod); or the diketonate of 2,2,6,6-tetramethyl-3,5-heptanedione (hdpm).

12. The method of claim 1, wherein each complex formed in step (b) volatizes at a temperature of about 250° C. or less.

13. The method of claim 1, further comprising collecting at least one separated complex.

14. The method of claim 1, wherein the ligand is a diketonate of 6,6,7,7,8,8-heptafluoro-2,2-dimethyl-3,5-octanedione (hfod).

15. The method of claim 1, wherein the sample comprises at least three different chemical elements selected from rare earth elements, actinides, and heavy transition metals.

16. The method of claim 3, wherein the ligand is a diketonate of 1,1,1,5,5,5-hexafluoroactylacetone (hfac).

17. The method of claim 1, wherein the method further comprises determining the identity of at least one or more chemical elements based upon a retention time of a volatized complex on a gas chromatography column or upon a temperature of volatization of a complex, thereby characterizing said sample.

18. The method of claim 6, wherein the method further comprises collecting at least one separated complex, thereby recovering at least one rare earth element.

19. The method of claim 7, wherein the method further comprises collecting at least one separated complex, thereby recovering at least one of said at least two chemical elements from the sample comprising nuclear fission and/or activation products or from the sample comprising waste from electronic and/or high technology products.

* * * * *